(12) United States Patent
Milligan et al.

(10) Patent No.: US 9,181,554 B2
(45) Date of Patent: Nov. 10, 2015

(54) METHODS FOR DETECTING A TARGET NUCLEOTIDE SEQUENCE IN A SAMPLE UTILISING A NUCLEASE-APTAMER COMPLEX

(75) Inventors: Andrew Simon Milligan, Bridgewater (AU); Stephen John Fletcher, Mylor (AU)

(73) Assignee: Australian Centre for Plant Functional Genomics Pty, Ltd, Urrbae, South Australia (AU)

( * ) Notice: Subject to any disclaimer, the term of this patent is extended or adjusted under 35 U.S.C. 154(b) by 1308 days.

(21) Appl. No.: 12/594,342

(22) PCT Filed: Apr. 4, 2008

(86) PCT No.: PCT/AU2008/000496
§ 371 (c)(1),
(2), (4) Date: Mar. 26, 2010

(87) PCT Pub. No.: WO2008/122088
PCT Pub. Date: Oct. 16, 2008

(65) Prior Publication Data
US 2010/0291561 A1 Nov. 18, 2010

(30) Foreign Application Priority Data
Apr. 5, 2007 (AU) .............................. 2007901826

(51) Int. Cl.
*C12N 15/115* (2010.01)
*C12N 15/11* (2006.01)
*C12Q 1/68* (2006.01)

(52) U.S. Cl.
CPC ............ *C12N 15/115* (2013.01); *C12N 15/111* (2013.01); *C12Q 1/6816* (2013.01); *C12N 2310/3513* (2013.01); *C12N 2320/12* (2013.01); *G01N 2500/00* (2013.01)

(58) Field of Classification Search
USPC ............. 435/6.1, 6.18, 91.31; 536/23.1, 24.3, 536/24.5
See application file for complete search history.

(56) References Cited

U.S. PATENT DOCUMENTS

| | | | |
|---|---|---|---|
| 5,846,701 A * | 12/1998 | Kacian et al. ................. | 435/4 |
| 2002/0150996 A1 | 10/2002 | Nilsen-Hamilton | |
| 2006/0088864 A1 | 4/2006 | Smolke et al. | |

FOREIGN PATENT DOCUMENTS

| | | |
|---|---|---|
| EP | 1700912 A1 | 9/2006 |
| WO | WO 96/40159 | 12/1996 |
| WO | WO 00/28084 A1 | 5/2000 |
| WO | WO 00/79004 A1 | 12/2000 |
| WO | WO 2006/125094 A2 | 11/2006 |
| WO | WO 2007/032359 A1 | 3/2007 |
| WO | WO 2009/152566 A1 | 12/2009 |

OTHER PUBLICATIONS

Beyer et al, Adv. Sci. & Tech., vol. 53, pp. 116-121 (2006).*
Yoshida et al, Biochem. Biophys. Res. Comm., vol. 348, No. 1, pp. 245-252 (2006).*
Thiviyanathan et al, Biochem. Soc. Trans., vol. 35, No. 1, pp. 50-52 (2007).*
Breaker, R.R., Current Opinion in Biotech., vol. 13, pp. 31-39 (2002).*
Tucker et al., Current Opinion in Structural Biology, vol. 15, pp. 342-348 (2005).*
Fahlman et al, J. Am. Chem. Soc., vol. 124, pp. 4610-4616 (2002).*
Beyer et al (Nucleic Acids Res., vol. 34, No. 5, pp. 1581-1587 (2006)).*
Rusconi et al (Nature, vol. 419, pp. 90-94 (2002)).*
Biggins, J.B. et al.; "A continuous assay for DNA cleavage: the application of break lights to enediynes, iron-dependent agents, and nucleases"; 2000, *PNAS*, vol. 97, No. 5, pp. 13537-13542.
Fletcher, S.J. et al.; "Toward specific detection of Dengue virus serotypes using a navel modular biosensor"; 2010, *Biosensors and Bioelectronics*, vol. 26, No. 4, pp. 1696-1700.
Hamaguchi, N. et al.; "Aptamer beacons for the direct detection of proteins"; 2001, *Analytical Biochemistry*, vol. 294, No. 2, pp. 126-131.
Ikebukuro, K. et al.; "Novel electrochemical sensor system for protein using the aptamers in sandwich manner"; 2005 *Biosensors and Bioelectronics*, vol. 10, No. 10, pp. 2168-2172.
Kettling, U. et al.; "Real-Time Enzyme Kinetics Monitored by Dual-Color Fluorescence Cross-Correlation Spectroscopy"; 1998, *PNAS*, vol. 95, No. 4, pp. 1416-1420.
Silverman, S.K. et al.; "Rube Goldberg goes (ribo)nuclear? Molecular switches and sensors made from RNA"; 2003, *RNA, Cold Spring Harbor Laboratory Press*, vol. 9, No. 1, pp. 377-383.
Thiviyanathan, V. et al.; "Combinational selection and delivery of thioaptamers"; 2007, *Biochemical Society Transactions*, vol. 35, No. 1, pp. 50-52.
Yoshida, W. et al.; "Aptameric enzyme subunit for biosensing based on enzymatic activity measurement"; 2006, *Analytical Chemistry*, vol. 78, No. 10, pp. 3296-3303.
Yoshida, W. et al.; "Homogeneous DNA sensing using enzyme-inhibiting DNA aptamers"; 2006, *Biochemical and Biophysical Research Communications*, vol. 348, No. 1, pp. 245-252.
Beyer, S., et al., "A modular DNA signal translator for the controlled release of a protein by an aptamer," *Nucleic Acids Research*, vol. 34(5), pp. 1581-1587 (2006).
Beyer, S., et al., "Controlled Release of Thrombin using Aptamer-based Nanodevices," *Advances in Science and Technology*, vol. 53, pp. 116-121 (2006).

(Continued)

*Primary Examiner* — Jane Zara
(74) *Attorney, Agent, or Firm* — Klarquist Sparkman, LLP

(57) ABSTRACT

The present invention relates to methods for detecting a target nucleotide sequence in a sample. More particularly, the present invention relates to methods for detecting a target nucleotide sequence in a sample which utilise a nuclease-aptamer complex. The present invention also provides nuclease-binding aptamers, nuclease-aptamer complexes and linker molecules that may be used in accordance with the methods of the present invention.

12 Claims, 12 Drawing Sheets

(56) References Cited

OTHER PUBLICATIONS

Beyer et al., "Design Variations for an Aptamer-Based DNA Nanodevice," *J. Biomed. Nanotech.*, 1:96-101, 2005.

Pileur et al., "Selective inhibitory DNA aptamers of the human RNase H1," *Nucleic Acids Res.*, 31(19):5776-5788, 2003.

Somasunderam et al., "Combinatorial selection, inhibition, and antiviral activity of DNA thioaptamers targeting the RNase H domain of HIV-1 reverse transcriptase," *Biochemistry*, 44(30):10388-10395, 2005; doi:10.1021/bi0507074.

International Search Report issued in International Application No. PCT/AU2009/000768 on Jul. 27, 2009 (3 pages).

* cited by examiner

METHODS FOR DETECTING A TARGET NUCLEOTIDE SEQUENCE IN A SAMPLE UTILISING A NUCLEASE-APTAMER COMPLEX

PRIORITY CLAIM

The present application is a U.S. National Stage Application of PCT/AU2008/000496, filed 4 Apr. 2008, which claims priority to Australian provisional patent application 2007901826 filed on 5 Apr. 2007, the contents of which are herein incorporated by reference.

FIELD OF THE INVENTION

The present invention relates to methods for detecting a target nucleotide sequence in a sample. More particularly, the present invention relates to methods for detecting a target nucleotide sequence in a sample which utilise a nuclease-aptamer complex.

BACKGROUND OF THE INVENTION

A range of molecular technologies for the detection of a nucleotide sequence of interest (also referred to herein as a 'target nucleotide sequence') have been developed. Such methods have application in, for example, public health, the detection of pathogens in food or water, epidemiological studies, genetically modified organism (GMO) detection, medicine, clinical diagnoses, disease susceptibility diagnoses, tissue typing, blood screening, forensic medicine, bioweapon detection, molecular toxicology, gene therapy, and DNA tagging, among many other applications.

Current methods for detecting a target DNA sequence generally involve one, or a combination of, molecular techniques. These techniques generally fall into three groups loosely defined as sequence-specific detection, sequence-specific enrichment and signal amplification.

Most detection techniques gain their sequence specificity through base paring of complementary probes or oligonucleotides to a sequence of interest within the target DNA sample.

The two most commonly used DNA detection methods, polymerase chain reaction (PCR) and Southern blotting, differ in how they proceed from this point. The PCR method enriches a target DNA through a series of amplification cycles and signal detection can be, for example, though the use of stains, fluorescence or radiolabelling. Southern blotting involves no DNA enrichment step, but uses high-energy $^{32}P$ for signal amplification. These extensively used techniques, though highly developed, still retain significant drawbacks. For PCR, the equipment required is expensive, the process is time-consuming and the degree of expertise required is high. Southern blotting often uses hazardous radioactive labelling, takes up to a week to complete, and requires large amounts of substrate DNA.

An effective biosensor for detecting a specific DNA sequence in a sample that addresses one or more of the deficiencies of the currently available techniques, without substantially losing target-specificity or sensitivity, would be desirable. Furthermore, such a technique would also ideally require a low capital input (particularly in the case of equipment requirement), minimal expertise or technique-specific training, and provide quick and accurate results.

Reference to any prior art in this specification is not, and should not be taken as, an acknowledgment or any form of suggestion that this prior art forms part of the common general knowledge in any country.

SUMMARY OF THE INVENTION

The present invention is predicated in part on methods for the detection of a target nucleotide sequence in a sample, wherein the method utilises a nuclease-aptamer complex.

Accordingly, in a first aspect, the present invention provides a method for detecting a target nucleotide sequence in a sample, the method comprising:
 providing a nuclease-aptamer complex, the complex comprising a nuclease bound to an aptamer, wherein binding of the aptamer to the nuclease inhibits the activity of the nuclease and wherein inhibition of the nuclease's activity by the aptamer is directly or indirectly reduced or eliminated when the target nucleotide sequence is present in the sample;
 applying the nuclease-aptamer complex to the sample;
 detecting the activity of the nuclease, wherein increased nuclease activity is indicative of the presence of the target nucleotide sequence in the sample.

Nucleases are particularly useful as indicators in aptamer complexes, as many nucleases are highly active and may achieve a higher degree of signal amplification than other enzymes. Furthermore, a wide array of nucleases are available, many of which act on different nucleic acid substrates or specific nucleic acid sequences. This target specificity also allows the present invention to provide 'multiplex' detection methods which allow the simultaneous detection of a plurality of target sequences in a sample.

In some particular embodiments of the invention the nuclease may be a restriction endonuclease.

In one embodiment the method of the present invention may exploit hybridisation between the aptamer and the target nucleotide sequence in order to modify, reduce or eliminate binding between the nuclease and the aptamer. Thus, in one embodiment the method of the present invention may comprise the steps of:
 providing a nuclease-aptamer complex, the complex comprising a nuclease bound to an aptamer, wherein binding of the aptamer to the nuclease inhibits the activity of the nuclease and wherein the aptamer is able to hybridise to a target nucleotide sequence to modify, reduce or eliminate binding between the nuclease and the aptamer when the target nucleotide sequence is present in the sample;
 applying the nuclease-aptamer complex to the sample;
 allowing the target nucleotide sequence, if present in the sample, to hybridise with the aptamer; and
 detecting the activity of the nuclease wherein increased nuclease activity is indicative of the presence of the target nucleotide sequence in the sample.

In the above embodiment of the invention, the aptamer is designed or selected such that it comprises both a region which binds to the nuclease and a region which can hybridise to the target nucleotide sequence. However, in another embodiment of the invention, the necessity to design or select the aptamer to contain both a nuclease-binding region and a target nucleotide sequence binding region may be eliminated via the use of a linker nucleic acid.

Accordingly, in another embodiment, the method of the present invention comprises the steps of:
 providing a nuclease-aptamer complex, the complex comprising a nuclease bound to an aptamer, wherein binding of the aptamer to the nuclease inhibits the activity of the nuclease;

providing a linker nucleic acid comprising a first portion which can hybridise with the target nucleotide sequence if it is present in the sample, and a second portion which can hybridise with the aptamer when the first portion of the linker nucleic acid is hybridised to the target nucleotide sequence, wherein hybridisation between the aptamer and the second portion of the linker nucleic acid modifies, reduces or eliminates binding between the aptamer and the nuclease;

applying the nuclease-aptamer complex to the sample;

applying the linker nucleic acid to the sample;

allowing the first portion of the linker nucleic acid to hybridise with the target nucleotide sequence if it is present in the sample;

allowing the second portion of the linker nucleic acid to hybridise with the aptamer when the first portion of the linker nucleic acid hybridises with the target nucleotide sequence; and detecting the activity of the nuclease, wherein increased nuclease activity in the sample is indicative of the presence of the target nucleotide sequence in the sample.

The use of a nuclease-aptamer complex in the methods of the present invention also allow the methods of the present invention to be multiplexed, that is, the present invention also provides methods to simultaneously detect a plurality of target nucleotide sequences in a sample.

In a second aspect, the present invention provides a method of screening an organism for the presence of a target nucleotide sequence in the organism, the method comprising obtaining a nucleic acid-containing sample from the organism and determining the presence of the target nucleotide sequence in the sample according to the method of the first aspect of the invention.

In a third aspect, the present invention provides a nuclease-binding aptamer wherein binding of the aptamer to a nuclease inhibits the activity of the nuclease.

In a fourth aspect, the present invention also provides a nuclease-aptamer complex comprising a nuclease bound to an aptamer.

In a fifth aspect, the present invention comprises a linker nucleic acid comprising a first portion which can hybridise with a target nucleotide sequence, and a second portion which can hybridise with an aptamer in a nuclease-aptamer complex when the first portion of the linker nucleic acid is hybridised to the target nucleotide sequence, wherein hybridisation between the aptamer and the second portion of the linker nucleic acid modifies, reduces or eliminates binding between the aptamer and the nuclease in the nuclease-aptamer complex.

In a sixth aspect, the present invention provides a kit for performing any of the methods of the present invention, the kit comprising one or more of an aptamer according to the third aspect of the invention; a nuclease-aptamer complex according to the fourth aspect of the invention; and/or a linker nucleic acid according to the fifth aspect of the invention.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to herein by a sequence identifier number (SEQ ID NO:). The SEQ ID NOs: correspond numerically to the sequence identifiers in the sequence listing, eg. <400>1 (SEQ ID NO:1), <400>2 (SEQ ID NO: 2), etc. A summary of the sequence identifiers is provided in Table 2. A sequence listing is provided at the end of the specification.

TABLE 1

Summary of Sequence Identifiers

| Sequence Identifier | Sequence |
|---|---|
| SEQ ID NO: 1 | EcoRI-binding aptamer nucleotide sequence motif 1 |
| SEQ ID NO: 2 | EcoRI-binding aptamer nucleotide sequence motif 2 |
| SEQ ID NO: 3 | Aptamer 3_ADJ_L nucleotide sequence |
| SEQ ID NO: 4 | Aptamer 3_ADJ_L-binding nucleotide sequence |
| SEQ ID NO: 5 | CaMV 35S promoter targeting nucleotide sequence |
| SEQ ID NO: 6 | *Mycobacterium tuberculosis* targeting nucleotide sequence |
| SEQ ID NO: 7 | Arbitrary target-linker nucleotide sequence - FIG. 3A |
| SEQ ID NO: 8 | Arbitrary target nucleotide sequence - FIG. 3A |
| SEQ ID NO: 9 | 35S-linker nucleotide sequence - FIG. 3B |
| SEQ ID NO: 10 | 35S target nucleotide sequence - FIG. 3B |
| SEQ ID NO: 11 | *M. tuberculosis*-linker nucleotide sequence - FIG. 3C |
| SEQ ID NO: 12 | *M. tuberculosis* target nucleotide sequence - FIG. 3C |
| SEQ ID NO: 13 | Aptamer 1, Aptamer 40, and Aptamer 41 nucleotide sequences - FIG. 4B |
| SEQ ID NO: 14 | Aptamer 3 nucleotide sequence - FIG. 4B |
| SEQ ID NO: 15 | Aptamer 4 and Aptamer 28 nucleotide sequences - FIG. 4B |
| SEQ ID NO: 16 | Aptamer 7 nucleotide sequence - FIG. 4B |
| SEQ ID NO: 17 | Aptamer 8 and Aptamer 25 nucleotide sequences - FIG. 4B |
| SEQ ID NO: 18 | Aptamer 33 nucleotide sequence - FIG. 4B |
| SEQ ID NO: 19 | Arbitrary target nucleotide sequence - FIG. 5 |
| SEQ ID NO: 20 | EcoRI molecular break light (MBL) molecule - FIG. 7 |
| SEQ ID NO: 21 | Oligonucleotide library oligomer consensus sequence |
| SEQ ID NO: 22 | PCR primer - library amplification |
| SEQ ID NO: 23 | PCR primer - library amplification |

DESCRIPTION OF EXEMPLARY EMBODIMENTS

It is to be understood that the following description is for the purpose of describing particular embodiments only and is not intended to be limiting with respect to the above description.

In a first aspect, the present invention provides a method for detecting a target nucleotide sequence in a sample, the method comprising:

providing a nuclease-aptamer complex, the complex comprising a nuclease bound to an aptamer, wherein binding of the aptamer to the nuclease inhibits the activity of the nuclease and wherein inhibition of the nuclease's activity by the aptamer is directly or indirectly reduced or eliminated when the target nucleotide sequence is present in the sample;

applying the nuclease-aptamer complex to the sample;

detecting the activity of the nuclease, wherein increased nuclease activity is indicative of the presence of the target nucleotide sequence in the sample.

The "sample" in which a target nucleotide sequence may be detected may be any sample that putatively contains the target nucleotide sequence. For example, the sample may be a biological sample including samples derived from an organism, a sample containing one or more cells, a blood sample, a plasma sample, a CSF fluid sample, an amniotic fluid sample and the like; an environmental sample such as a water, air or soil sample; a food or beverage sample; and the like. The samples contemplated herein may be used in a crude form, or the samples may be processed for use in accordance with the present invention. For example, the sample may have one or more nucleic acid extraction or purification steps performed thereon in order to purify or semi-purify any nucleic acids present in the sample. Methods for the extraction and purification of nucleic acids from a range of samples would be readily ascertained by one of skill in the art. In this regard, reference is made to *The Nucleic Acid Protocols Handbook* (Rapley Ed. Humana Press, 2000).

As referred to herein, a "nuclease" should be understood as any enzyme that can cleave the sugar-phosphate backbone of a nucleic acid. As such, the term "nuclease" should be understood to encompass both endonucleases and exonucleases. Furthermore, the nucleases contemplated for use in accordance with the present invention may be deoxyribonucleases (which cleave DNA) or ribonucleases (which cleave RNA). Generally, the nuclease used in accordance with the present invention is a nuclease that, once inhibition by the aptamer has been reduced or eliminated, still cannot cleave or digest the target nucleotide sequence, but can cleave or digest another nucleotide sequence (such as a reporter nucleic acid—see later) such that the activity of the nuclease may be detected. Nucleases that may be used in accordance with the present invention include, for example, restriction endonucleases, nucleases that cleave at sequence mis-matches, S1 nuclease, T7 endonuclease I, T4 endonuclease VII, CEL I (a plant-specific extracellular glycoprotein that belongs to the S1 nuclease family), and ribonucleases such as RNases A & H.

However, in some particular embodiments of the invention (as set out later) the nuclease may be a restriction endonuclease.

The term "aptamer", as referred to herein, should be understood as a nucleic acid molecule, at least a portion of which is able to bind to another molecule.

Nucleic acid aptamers are generally single-stranded nucleic acid molecules with complex secondary or tertiary structures (which as discussed later may include double-stranded portions or regions) that can specifically bind a target molecule with high affinity. When bound to enzymes, certain aptamers are able to reduce or inhibit their enzymatic activity. Generally, the aptamers contemplated by the present invention can bind at least to a nuclease, and thus alter the activity of the nuclease. Furthermore, the nuclease-binding aptamers contemplated by the present invention generally reduce or eliminate the activity of the nuclease when bound thereto. The aptamers of the present invention may also comprise a region which does not bind to the nuclease. This region, or the nuclease binding region itself, may also exhibit binding affinity toward another molecule such as a target nucleotide sequence or linker nucleic acid (as described later).

The aptamers contemplated for use in accordance with the present invention may be any suitable nucleic acid or equivalent thereof. In this regard, the aptamers may comprise, for example, DNA, RNA, a nucleic acid mimic such as Peptide Nucleic Acid (PNA) or Locked Nucleic Acid (LNA), DNA or RNA comprising one or more modified nucleotides, and the like. "Modified" nucleotides include, for example, nucleotides having chemical modifications to any of the phosphate backbone, sugar moiety or base moiety of the nucleotide, tritylated bases and unusual bases such as inosine. The use of modified nucleotides may also affect the binding characteristics of the aptamer to the nuclease, for example as described in Latham et al. (*Nucl Acids Res* 22(14): 2817-2822, 1994).

In some specific embodiments RNA aptamers may be used, since RNA can form secondary structures that DNA generally does not, such as pseudoknots and base triples.

Nucleic acid aptamers may also be modified, for example to increase stability, in a number of ways including, for example:

(i) Synthesis of aptamers using L-nucleotides (the mirror image of natural nucleotides) so that they cannot be degraded by naturally occurring nucleases;
(ii) Incorporation of locked nucleic acid (LNA) and/or peptide nucleic acid (PNA) residues into the aptamer. LNAs and PNAs also increase stability of nucleic acid duplexes;
(iii) Other chemical modifications of ribonucleotides, such as 2'-amino- and 2'-fluoro-pyrimidine nucleotides or 2'-O-methyl nucleotides; and/or
(iv) Capping at the 3' end with a deoxythymidine to increase resistance to exonuclease degradation.

Nucleic acid aptamers that bind to, and inhibit the activity of, a particular protein (such as a nuclease) may be produced using methods known in the art. For example, in-vitro selection methods (eg. see Ellington and Szostak, *Nature* 346 (6287): 818-22, 1990) and SELEX methods (eg. see Tuerk and Gold, *Science* 249(4968): 505-510, 1990) may be used. Further details relating to the production and selection of aptamers may also be found in the review of Osborne and Ellington (*Chem Rev* 97(2): 349-370, 1997).

In light of the above, a "nuclease-aptamer complex" should be understood as a nuclease to which an aptamer is bound, or a nuclease and aptamer which may become bound under the conditions under which the method of the invention is performed, such that binding of the aptamer to the nuclease inhibits the activity of the nuclease and inhibition of the nuclease's activity by the aptamer is directly or indirectly reduced or eliminated when the target nucleotide sequence is present in the sample.

In some embodiments of the invention the presence of the target nucleotide sequence in the sample modifies, reduces or eliminates binding between the nuclease and the aptamer, thereby reducing or eliminating inhibition of the nuclease's activity by the aptamer.

As referred to herein modification, reduction or elimination of binding between the nuclease and the aptamer refers to any qualitative or quantitative change in the nature of the binding between the aptamer and the nuclease which brings about a reduction or elimination of inhibition of the nuclease's activity by the aptamer. Such changes may arise as a result of binding between the aptamer and another molecule such as the target nucleotide sequence or a linker nucleic acid or binding between the nuclease-aptamer complex and another molecule such as the target nucleotide sequence or a linker nucleic acid.

"Qualitative or quantitative changes" in the nature of the binding between the aptamer and the nuclease may include, for example: a change in the binding strength between the nuclease and the aptamer; a change in the interaction or binding sites on the nuclease and/or aptamer; dissociation of the nuclease-aptamer complex, optionally with binding of the aptamer to another molecule; a change in the conformation, secondary structure or tertiary structure of the aptamer or nuclease which reduces the level of inhibition of the nuclease by the aptamer; a change in the relative positions of the binding sites on the aptamer and/or nuclease; and the like.

In one embodiment the method of the present invention may exploit hybridisation between the aptamer and the target nucleotide sequence in order to modify, reduce or eliminate binding between the nuclease and the aptamer.

Thus, in one embodiment the method of the present invention may comprise the steps of:
providing a nuclease-aptamer complex, the complex comprising a nuclease bound to an aptamer, wherein binding of the aptamer to the nuclease inhibits the activity of the nuclease and wherein the aptamer is able to hybridise to a target nucleotide sequence to modify, reduce or eliminate binding between the nuclease and the aptamer when the target nucleotide sequence is present in the sample;

applying the nuclease-aptamer complex to the sample;

allowing the target nucleotide sequence, if present in the sample, to hybridise with the aptamer; and detecting the activity of the nuclease wherein increased nuclease activity is indicative of the presence of the target nucleotide sequence in the sample.

In this embodiment of the invention, the aptamer is able to hybridise to the target nucleotide sequence to modify, reduce or eliminate binding between the nuclease and the aptamer. Hybridisation between the target nucleotide sequence and the aptamer, together with concomitant modification, reduction or elimination of binding between the nuclease and aptamer, may occur under the initial conditions of the sample or, alternatively, the conditions may be modified to allow or promote binding between the aptamer and the target nucleotide sequence (if it is present in the sample).

For example, binding between the aptamer and the target nucleotide sequence and/or binding between the aptamer and nuclease may be modulated by altering the salt concentration and/or temperature. In addition, destabilising agents such as formamide may also be used to modulate the binding of the aptamer to any of the nuclease, the target nucleotide sequence and/or a linker nucleic acid.

In this embodiment of the invention, the aptamer should be designed or selected such that it comprises both a region which binds to the nuclease and a region which can hybridise, at least under some hybridisation conditions, to the target nucleotide sequence. These regions may be separated by one or more nucleotide residues, partially overlapping, completely overlapping or one region may be contained within the other.

However, in another embodiment of the invention, the necessity to design or select the aptamer to contain both a nuclease-binding region and a target nucleotide sequence binding region may be eliminated via the use of a linker nucleic acid.

Accordingly, in another embodiment, the method of the present invention comprises the steps of:
providing a nuclease-aptamer complex, the complex comprising a nuclease bound to an aptamer, wherein binding of the aptamer to the nuclease inhibits the activity of the nuclease;
providing a linker nucleic acid comprising a first portion which can hybridise with the target nucleotide sequence if it is present in the sample, and a second portion which can hybridise with the aptamer when the first portion of the linker nucleic acid is hybridised to the target nucleotide sequence, wherein hybridisation between the aptamer and the second portion of the linker nucleic acid modifies, reduces or eliminates binding between the aptamer and the nuclease;
applying the nuclease-aptamer complex to the sample;
applying the linker nucleic acid to the sample;
allowing the first portion of the linker nucleic acid to hybridise with the target nucleotide sequence if it is present in the sample;
allowing the second portion of the linker nucleic acid to hybridise with the aptamer when the first portion of the linker nucleic acid hybridises with the target nucleotide sequence; and
detecting the activity of the nuclease, wherein increased nuclease activity in the sample is indicative of the presence of the target nucleotide sequence in the sample.

In one embodiment, the linker nucleic acid comprises a stem loop structure and at least a portion of the first portion of the linker is comprised within a loop of the stem-loop structure and at least a portion of the second portion of the linker is comprised within a stem of the stem-loop structure.

In one embodiment, the second portion of the linker (ie. the aptamer-binding portion) is generally of a length sufficient to enable denaturation or dissociation of the stem portion when the linker binds to the target nucleotide sequence. That is, hybridisation of the first portion of the linker (at least partially comprised within the loop region of the stem loop) generally effects denaturation or dissociation of the stem portion of the linker, thus exposing the aptamer-binding region(s) of the linker nucleic acid. In light of the above, the stem-portion of the stem loop structure generally comprises at least 5 nucleotides and may extend to about 50 nucleotides in length. However, the present invention should not be considered limited to any specific length of sequence and other sequence lengths may be used that provide the functionality described above.

In another embodiment, the linker is designed such that the melting temperature of the first portion of the linker, when hybridised to the target, is higher than the melting temperature of the stem of the linker. In some embodiments, the melting temperature of the first portion of the linker when hybridised to the target is about 1° C., about 2° C., about 3° C., about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C. or about 20° C. higher than the melting temperature of the stem of the linker. In one specific embodiment, the melting temperature of the first portion of the linker when hybridised to the target is about 10° C. higher than the melting temperature of the stem of the linker.

In this embodiment, when the target nucleotide sequence is present in the sample, a heat or chemically denatured linker binds to the target in preference to reverting to its native stem/loop structure following heat or chemical denaturation followed by the introduction of renaturation conditions.

The stem-portion of the stem-loop structure may be completely homologous, ie. no mismatches in the hybridising sequences. Alternatively, the stem portion may include one or more mis-matched base pairs. For example, mis-matches may be useful in promoting denaturation of the stem portion of the stem loop structure during the method of the present invention and/or to allow hybridisation between the aptamer and the stem portion. Features such as mismatches and/or overhangs may also be incorporated into the stem to provide an appropriate melting temperature difference to be obtained without the requirement for an excessively long target-complementary sequence.

In further embodiments, the first portion may not be wholly within the loop, and may also be part of the stem. Similarly, the second portion may not necessarily be wholly contained within the stem portion, and may extend into the loop portion In further embodiments, the first and second portions of the linker may be separated by one or more nucleotide residues, partially overlapping, completely overlapping or one region may be contained within the other.

The use of a linker nucleic acid in accordance with this embodiment of the invention also provides a significant advantage in that it removes the requirement to design or select the aptamer to have a target nucleotide sequence binding region. Rather, the target nucleotide sequence binding region can be incorporated into the first portion of the linker and the second portion of the linker may be designed to bind to the aptamer. This provides an advantage in that incorporation of an aptamer-binding nucleotide sequence into a linker nucleic acid is simpler and/or less time-consuming than having to design or select an aptamer to include both a nuclease-binding region and a target binding region. That is, the linker nucleic acid may be designed such that it binds to an aptamer that binds to a nuclease rather than having to select an aptamer on the basis of the ability to bind to both a nuclease and a target nucleotide sequence. Another significant advantage is that a single nuclease-aptamer complex may be applied to the detection of many different targets, simply by modifying the first portion of the linker.

As set out above, the methods of the present invention involve detecting the activity of the nuclease, wherein increased nuclease activity is indicative of the presence of the target nucleotide sequence in the sample.

The method used for detecting the activity of the nuclease may be any suitable method for the subject nuclease. For example, the activity of a DNase or RNase may be ascertained by observing degradation or cleavage of a DNA, RNA or DNA/RNA hybrid reporter nucleic acid, respectively. The reporter nucleic acid may be single-stranded or double-stranded, as appropriate for the activity of the nuclease. Cleavage of the reporter nucleic acid may be detected by any known method. For example, cleavage of a reporter nucleic acid into a lower molecular weight product may be determined by electrophoretic methods, staining methods, the release of a labelled nucleotide, cleavage of a fluorophore/quencher labelled nucleic acid to release a fluorophore, and the like.

As set out above, in some specific embodiments, the nuclease used in accordance with the present invention is a restriction endonuclease. As referred to herein, a "restriction endonuclease" refers to any endonuclease that binds to double-stranded DNA at a specific nucleotide sequence and then, if both strands of the DNA lack appropriate modification at that sequence, cleaves the DNA either at the recognition sequence or at another site in the DNA molecule. A wide array of restriction endonucleases with different recognition sites and different cleavage sites would be readily ascertained by one of skill in the art. For example, a range of restriction endonucleases may be sourced from New England Biolabs (Ipswich, Mass., USA).

In the embodiments of the invention utilising a restriction endonuclease, the activity of the restriction endonuclease may be determined by the rate or extent of cleavage of a reporter nucleic acid which comprises at least a region of double stranded DNA.

In one specific embodiment, a fluorophore is bound to the reporter nucleic acid and a quencher, which quenches the fluorescence of the fluorophore, is also bound to the reporter nucleic acid, wherein cleavage of the reporter nucleic acid by the nuclease reduces or eliminates the quenching of the fluorophore by the quencher.

Exemplary fluorophores and quenchers would be readily ascertained by one of skill in the art. In this regard, reference is made to the review of Marras (*Methods Mol Biol* 335, 3-16, 2006).

In one specific embodiment, the reporter nucleic acid comprising a fluorophore and quencher may comprise a molecular break light (MBL) as described by Biggins et al. (*Proc Natl Acad Sci USA*. 97(25): 13537-13542, 2000).

In another exemplary embodiment, a polypeptide is bound to the reporter nucleic acid and an immobilisable agent is bound to the reporter nucleic acid, wherein cleavage of the reporter nucleic acid releases the polypeptide from the immobilisable agent; such that after cleavage of the reporter nucleic acid and immobilisation of the immobilisable agent, the amount of non-immobilised polypeptide is indicative of the activity of the nuclease.

A wide array of "immobilisable agents" would be readily ascertained by one of skill in the art and may include, for example:

(i) an antigen, which may be immobilised by contacting with an immobilised antibody that can bind the antigen;
(ii) an antibody, which may be immobilised by contacting with an immobilised antigen or anti-idiotypic antibody that can bind the antibody;
(iii) a polypeptide comprising a histidine tag, which may be immobilised by contacting an affinity medium comprising nickel or cobalt ions;
(iv) biotin, which may be immobilised by contacting with immobilised avidin or streptavidin;
(v) avidin or streptavidin, which may be immobilised by contacting with immobilised biotin; and/or
(vi) a magnetic or paramagnetic particle, which may be immobilised via a magnetic field.

As set out above, some immobilisable agents may be immobilised by contacting the immobilisable agent with a binding partner that is itself immobilised. The immobilisation of the binding partner may be achieved using any means known in the art. For example, the binding partner of the immobilisable agent may be immobilised onto a surface of a culture vessel, tube or plate (which may have been pre-treated with an agent such as a silane), immobilised onto the surface of a bead or other particle, immobilised onto a column or other chromatography medium, or immobilised onto a membrane.

A range of other immobilisable agents would also be readily ascertained by one of skill in the art, and the present invention should not be considered in any way limited to the immobilisable agents exemplified above.

In one specific embodiment, the immobilisable agent is a magnetic bead and immobilisation of the immobilisable agent is effected by the application of a magnetic field to the sample.

After immobilisation of the immobilisable agent, any polypeptide remaining "free" in the sample may be detected using any standard methods of protein detection, as are known in the art such as electrophoresis, immunochromatographic tests, including lateral flow strips, western blotting, mass spectroscopy, detection using a biosensor (for a review of biosensor-based detection of proteins in solution see Leca-Bouvier and Blum, *Analytical Letters* 38(10): 1491-1517, 2005). A range of exemplary protein detection methods may be found in *Proteins and Proteomics: A Laboratory Manual* (Simpson, CSHL Press, 2003).

The use of a nuclease-aptamer complex in the methods of the present invention also allow the methods of the present invention to multiplexed, that is, the present invention also provides methods to simultaneously detect a plurality of target nucleotide sequences in a sample.

For example, in the embodiments of the invention wherein the aptamer binds to the target nucleotide sequence, a method for simultaneously detecting a plurality of target nucleotide sequences in a sample may comprise providing a plurality of nuclease-aptamer complexes, wherein at least two of the nuclease-aptamer complexes comprise: (i) aptamers which hybridise to different target nucleotide sequences; and (ii) different nucleases, the activity of which may be separately detected.

In the embodiments of the invention wherein the aptamer binds to a linker nucleic acid, a method for simultaneously detecting a plurality of target nucleotide sequences in a sample may comprise:

providing a plurality of linker nucleic acids at least two of which comprise different first portions which can hybridise to different target nucleotide sequences and also comprise different second portions which can hybridise with different aptamers; and providing a plurality of nuclease-aptamer complexes, wherein at least two of the nuclease-aptamer complexes comprise aptamers which preferentially hybridise to the different second portions of the linker nucleic acids and comprise different nucleases, the activity of which may be separately detected.

In another embodiment, a single nuclease aptamer complex may be used to detect the presence of one or more of a plurality of different targets in a sample. That is, in an embodiment of the invention wherein the aptamer binds to a linker nucleic acid, a method for simultaneously detecting a plurality of target nucleotide sequences in a sample may comprise:

providing a plurality of linker nucleic acids at least two of which comprise different first portions which can hybridise to different target nucleotide sequences but wherein the linker nucleic acids comprise second portions which can hybridise to the same aptamer; and providing a nuclease-aptamer complex comprising an aptamer which can hybridise with the second portions of the linker nucleic acids;

In the above embodiment, an increase in nuclease activity is indicative of the presence of one or more of the target nucleotide sequences in the sample.

As set out above, some embodiments of the methods of the present invention for simultaneously detecting a plurality of target nucleotide sequences are predicated, in part, on the use of a plurality of nuclease-aptamer complexes wherein at least two of the nuclease-aptamer complexes comprise different nucleases, the activity of which may be separately detected.

As referred to herein "different nucleases, the activity of which may be separately detected" refers to, for example, nucleases which act to cleave or digest distinguishable reporter nucleic acids. For example, one nuclease may cleave or digest RNA, while another may cleave or digest DNA.

In another embodiment, a plurality of reporter nucleic acids are provided, at least two of which comprise different nucleotide sequences that represent recognition and/or cleavage sites for different restriction endonucleases.

The cleavage of different reporter nucleic adds may be detected by, for example, electrophoretic methods, the release of a labelled nucleotide, cleavage of a fluorophore/quencher labelled nucleic acid to release a fluorophore, and the like, with the proviso that it is possible to distinguish the cleavage of one reporter nucleic acid from another.

For example, in one embodiment the reporter nucleic acids for the different nucleases comprise fluorophores that can be separately detected when released from a quencher.

In another embodiment the reporter nucleic acids for the different nucleases comprise polypeptides that can be separately detected when released from an immobilisable agent.

Polypeptides "that can be separately detected when released from an immobilisable agent" include, for example, polypeptides of different molecular mass which may be resolved by electrophoresis or mass spectroscopy, polypeptides having different charge which may be resolved by isoelectric focusing, polypeptides with different antigenicity that may be resolved by differences in antibody-binding activity, polypeptides with different enzymic activity that may be resolved by one or more enzymic activity assays, polypeptides that have one or more distinct physical characteristics (such as fluorescence at a particular wavelength) that allows resolution of polypeptides having different physical characteristics, polypeptides that incorporate one or more distinct detectable labels such as a radiolabel, chemical label or fluorescent label, and the like.

In a second aspect, the present invention provides a method of screening an organism for the presence of a target nucleotide sequence in the organism, the method comprising obtaining a nucleic acid sample from the organism and determining the presence of the target nucleotide sequence in the sample according to the method of the first aspect of the invention.

The method of the second aspect of the invention may be used to detect any target nucleotide sequence in a nucleic acid sample derived from an organism. For example, the target nucleotide sequence may be a nucleotide sequence that is endogenous or native to the organism or, alternatively, the target nucleotide sequence may be an introduced or exogenous nucleotide sequence. As such, target nucleotide sequences that may be detected using the method of the second aspect of the invention include, for example, genomic nucleotide sequences, transgenes, allele nucleotide sequences, single nucleotide polymorphisms, mutant nucleotide sequences, transposon nucleotide sequences or viral nucleotide sequences.

The method of the second aspect of the invention may be applied to the detection of a target nucleotide sequence in any organism. However, in one specific embodiment, the method of the second aspect of the invention may be used to detect a target nucleotide sequence in a nucleic acid sample derived from a plant. In the context of this embodiment of the invention, the nucleic acid sample derived from a plant should be understood to include a sample from a live plant (or part thereof such as an organ, tissue or cell) or a sample taken from a plant or part thereof which has been processed, such as a plant part processed for use as a food (eg. flours and the like).

The detection of specific nucleotide sequences in plants has particular application in, for example, the diagnosis of plant diseases, detection of food contamination, taxonomic identification of plants or plant varieties and the detection of genetically modified plants (either environmentally or in plants processed for food).

In one particular embodiment, the present invention has application for the detection of genetically modified plants in foodstuffs. In this regard, it has been recognised that at least one of the Cauliflower Mosaic Virus 35S promoter, the *Agrobacterium tumefaciens* nopaline synthase terminator and the 5-enolpyruvylshikimate-3-phosphate synthase (EPSPS) encoding nucleotide sequence are found in more that 95% of the presently available genetically modified crop plants. Thus, these sequences represent particularly valuable targets for the detection of genetically modified plant material.

Thus, in one specific embodiment of the second aspect of the invention, the target nucleotide sequence comprises one or more of: a Cauliflower Mosaic Virus 35S (CaMV 35S) promoter sequence, an *Agrobacterium tumefaciens* nopaline synthase (nos) terminator sequence or a 5-enolpyruvylshikimate-3-phosphate synthase (EPSPS) encoding nucleotide sequence.

In a third aspect, the present invention also provides a nuclease-binding aptamer. Generally, the nuclease-binding aptamers of the third aspect of the invention effect inhibition of the activity of a nuclease when bound to the nuclease.

The aptamers of the present invention can be generated by known aptamer generation or selection methods as previously described.

In some embodiments, the aptamers of the present invention can bind to and/or inhibit the activity of a restriction endonuclease and comprise a modified restriction endonuclease recognition sequence. The term "modified restriction endonuclease recognition sequence" should be understood as a nucleotide sequence within the aptamer that allows a restriction endonuclease to bind to the aptamer, but which is sufficiently different to the restriction endonuclease's native recognition sequence that the aptamer is not itself a substrate for cleavage by the restriction endonuclease.

In some embodiments, the modified restriction endonuclease recognition sequence may comprise a double stranded region of the aptamer that comprises a native recognition sequence for a restriction endonuclease with one or more of the following modifications:
(i) one or more nucleotide substitutions in one or both strands relative to the nucleotide sequence of the native recognition sequence;
(ii) one or more nucleotide pair mismatches in the modified recognition sequence;
(iii) one or more double-stranded insertions or deletions relative to the native recognition sequence; and/or
(iv) one or more insertions or deletions in one or both strands of the modified recognition sequence thus forming a loop structure comprising one or more unpaired nucleotides in one or both strands of the double stranded region.

The modified restriction endonuclease recognition sequence may comprise one or more modifications relative to a native recognition sequence. For example, 1, 2, 3, 4, 5, 6, 7, 8, 9, 10 or more modifications may be made depending on the nature and length of the native recognition sequence to be modified. However, in practice, the number of modifications would be limited to the number of modifications tolerated while the aptamer retains the ability to bind to the restriction endonuclease.

In one specific embodiment, the modified restriction endonuclease recognition sequence comprises a single nucleotide substitution relative to an endonuclease's native recognition sequence. In another specific embodiment, the modified restriction endonuclease recognition sequence comprises a single stranded deletion relative to a native endonucleases recognition sequence thus forming a loop structure comprising a single unpaired nucleotide residue in the opposite strand of the modified endonuclease recognition sequence. In a further embodiment, the single unpaired nucleotide residue in the loop structure is substituted relative to the native recognition sequence.

In one embodiment, the nuclease-binding aptamer binds to EcoRI and inhibits the activity of EcoRI when bound thereto.

In one embodiment, the EcoRI-binding aptamer of the present invention includes the nucleotide sequence motif:

```
5'-GAGTTC-3'        (SEQ ID NO: 1)
```

In a further embodiment, the EcoRI-binding aptamer of the present invention may also include the nucleotide sequence motif:

```
5'-HSGAGTTCWR-3'    (SEQ ID NO: 2)
``` wherein H may be any of A, T or C; S may be C or G; W may be A or T; and R may be A or G.

In a yet further embodiment, the EcoRI-binding aptamer of the present invention includes a modified EcoRI recognition sequence as set out below:

```
5'-GAGTTC-3'

3'-CT-AAG-5'
``` wherein the G residue shown in bold is an unpaired nucleotide residue forming a loop structure.

In a yet further embodiment, the EcoRI-binding aptamer may comprise the nucleotide sequence set forth in SEQ ID NO: 3 or a variant thereof which retains the ability to bind to and inhibit the activity of EcoRI. Typically, the contemplated variants comprise the nucleotide sequence motifs set forth in SEQ ID NO: 1 and/or SEQ ID NO: 2 and/or comprise the modified EcoRI recognition sequence as set out above.

In a fourth aspect, the present invention also provides a nuclease-aptamer complex comprising a nuclease bound to an aptamer. Generally, binding of the aptamer to the nuclease inhibits the activity of the nuclease in the nuclease-aptamer complex.

In some embodiments, the nuclease-aptamer complex may comprise a restriction endonuclease bound to an aptamer. In these embodiments, the aptamer in the nuclease-aptamer complex may comprise a modified restriction endonuclease recognition sequence as described above.

In a specific embodiment, the nuclease-aptamer complex comprises an EcoRI-aptamer complex. In this embodiment, the aptamer in the EcoRI-aptamer complex may be a EcoRI-binding aptamer as described above.

As will be appreciated, the present invention also extends to methods for the detection of a target nucleotide sequence as described earlier wherein the nuclease-aptamer complex is a nuclease-aptamer complex as described with respect to the fourth aspect of the invention.

In a fifth aspect, the present invention also comprises a linker nucleic acid comprising a first portion which can hybridise with a target nucleotide sequence, and a second portion which can hybridise with an aptamer in a nuclease-aptamer complex when the first portion of the linker nucleic acid is hybridised to the target nucleotide sequence, wherein hybridisation between the aptamer and the second portion of the linker nucleic acid modifies, reduces or eliminates binding between the aptamer and the nuclease in the nuclease-aptamer complex.

In one embodiment, the linker nucleic acid comprises a stem loop structure and at least a portion of the first portion of the linker is comprised within a loop of the stem-loop structure and at least a portion of the second portion of the linker is comprised within a stem of the stem-loop structure.

In another embodiment, the linker is designed such that the melting temperature of the first portion of the linker, when hybridised to the target, is higher than the melting temperature of the stem of the linker as hereinbefore described.

In one specific embodiment, the linker comprises a second portion which can hybridise with an EcoRI-binding aptamer as previously described. In a further specific embodiment, the second portion of the linker, which can hybridise with an EcoRI-binding aptamer, comprises the nucleotide sequence set forth in SEQ ID NO: 4.

The first portion of the linker may be adapted to bind to any target nucleotide sequence of interest. In one exemplary embodiment, the first portion of the linker molecule is adapted to hybridise to a region of the Cauliflower Mosaic Virus 35S promoter nucleotide sequence. In a more specific embodiment, the first portion of the linker molecule that is adapted to hybridise to a region of the Cauliflower Mosaic Virus 35S promoter nucleotide sequence comprises the nucleotide sequence set forth in SEQ ID NO: 5.

In another exemplary embodiment, the first portion of the linker molecule is adapted to hybridise to a *Mycobacterium tuberculosis* derived nucleotide sequence. In a more specific embodiment, the first portion of the linker molecule that is adapted to hybridise to a *Mycobacterium tuberculosis* derived nucleotide sequence comprises the nucleotide sequence set forth in SEQ ID NO: 6.

As will be appreciated, the present invention also extends to methods for the detection of a target nucleotide sequence as described earlier wherein the linker nucleic acid is a linker nucleic acid as described with respect to the fifth aspect of the invention.

In a sixth aspect, the present invention provides a kit for performing any of the methods of the present invention, the kit comprising one or more of an aptamer according to the third aspect of the invention; a nuclease-aptamer complex according to the fourth aspect of the invention; and/or a linker nucleic acid according to the fifth aspect of the invention.

Finally, reference is made to standard textbooks of molecular biology that contain methods for carrying out basic techniques encompassed by the present invention, including DNA restriction and ligation for the generation of the various genetic constructs described herein. See, for example, Maniatis et al., *Molecular Cloning: A Laboratory Manual* (Cold Spring Harbor Laboratory Press, New York, 1982) and Sambrook et al. (2000, supra).

The present invention is further described by the following non-limiting examples:

EXAMPLE 1

Method for Detecting a Target Nucleotide Sequence

A method according to one embodiment of the invention will be described with respect to FIG. 1.

Figure 1:
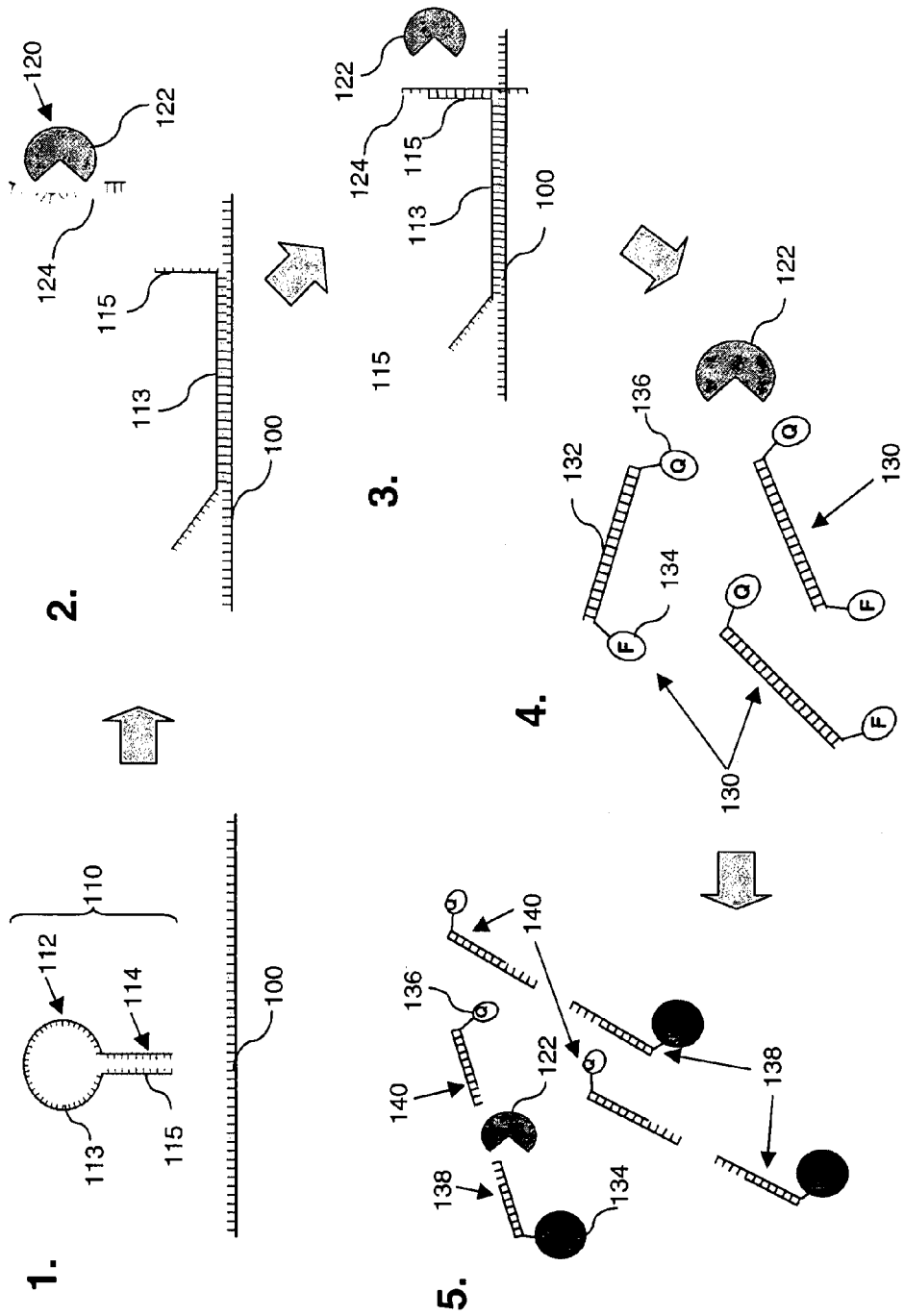
FIG. 1 is a schematic representation of a method for detecting a target nucleotide sequence in a sample according to one embodiment of the present invention.

Panel 1 of FIG. 1 shows a target nucleotide sequence 100 and a linker nucleic acid 110 comprising a stem-loop structure. The loop-portion 112 of the stem-loop structure comprises a first nucleotide sequence 113 that can hybridise with the target nucleotide sequence 100, and the stem-portion 114 comprises a second nucleotide sequence 115 to which an aptamer can bind when the first nucleotide sequence 113 has hybridised with the target nucleotide sequence 100.

Panel 2 shows hybridisation between the first nucleotide sequence 113 in the linker nucleic acid 110, and the target nucleotide sequence 100. This hybridisation causes the stem portion 114 of the stem-loop structure to dissociate and thus expose second nucleotide sequence 115 and make it available for binding with the aptamer 124 of a nuclease-aptamer complex 120.

Panel 3 shows hybridisation between the aptamer 124 and the second nucleotide sequence 115. This hybridisation reduces or eliminates inhibition of the nuclease 122 by the aptamer 124. In the figure, this reduction or elimination of inhibition is shown as separation of the aptamer 124 and nuclease 122, in part as a conceptual aid. However, as hereinbefore described, a reduction or elimination of inhibition of the nuclease 122 by the aptamer 124 may or may not involve actual dissociation between the nuclease 122 and the aptamer 124.

In panel 4, the activity of the nuclease 122, freed from inhibition by the aptamer 124, can be detected by cleavage of a reporter nucleic acid 130 by the nuclease 122. The reporter nucleic acid 130 comprises a nucleotide sequence 132 that is cleavable by the nuclease 122. The reporter nucleic acid 130 also comprises a bound fluorophore 134 and a bound quencher 136 that serves to quench the fluorescence of the fluorophore 134.

As shown in panel 5, however, cleavage of the reporter nucleic acid 130 into a fluorophore-containing fragment 138 and a quencher containing fragment 140, reduces or eliminates quenching of the fluorophore 134 by the quencher 136. Thus, cleavage of the reporter nucleic acid 130 by the nuclease 122 leads to the detection of a fluorescent signal from fluorophore 134.

EXAMPLE 2

Method for Simultaneously Detecting a Plurality of Target Nucleotide Sequences

A method according to another embodiment of the invention will be described with respect to FIG. 2.

Figure 2:
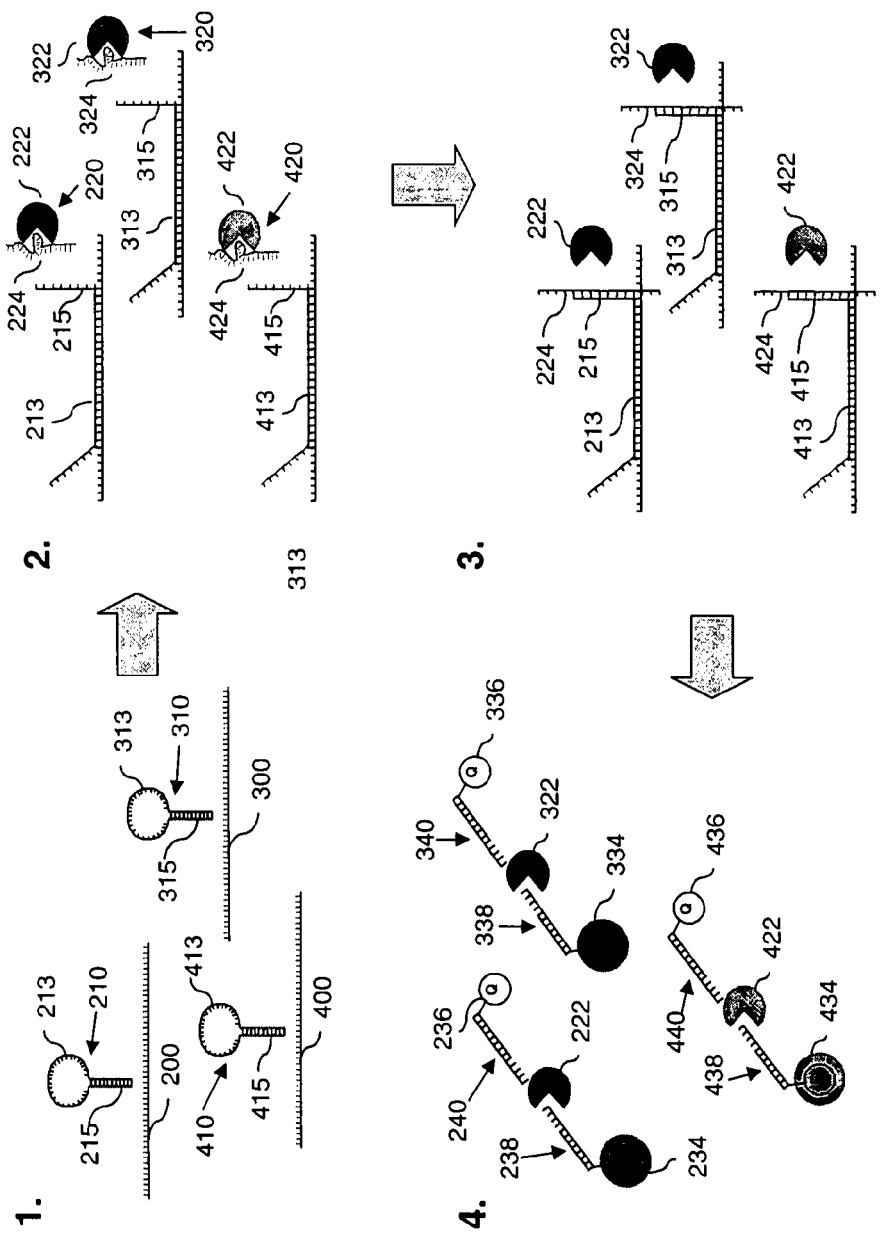
FIG. 2 is a schematic representation of a method for simultaneously detecting a plurality of target nucleotide sequences in a sample according to another embodiment of the present invention.

Panel 1 of FIG. 2 shows three different target nucleotide sequences 200/300/400, and three linker nucleic acids 210/310/410, each comprising a stem-loop structure. The loop-portions of the stem-loop structures each comprise a first nucleotide sequence 213/313/413 that can hybridise with one of the specific target nucleotide sequences 200/300/400. Specifically, first nucleotide sequence 213 can specifically hybridise with target nucleotide sequence 200, first nucleotide sequence 313 can specifically hybridise with target nucleotide sequence 300 and first nucleotide sequence 413 can specifically hybridise with target nucleotide sequence 400. The stem-portions of the linker nucleic acids each comprise a second nucleotide sequence 215/315/415 to which specific aptamers can specifically bind when the first nucleotide sequences 213/313/413 have hybridised with the target nucleotide sequences 200/300/400.

Panel 2 shows hybridisation between the first nucleotide sequences 213/313/413 and the target nucleotide sequences 200/300/400. This hybridisation causes the stem portions of the stem-loop structures to dissociate and thus expose second nucleotide sequences 215/315/415 and make them available for binding with the aptamers 224/324/424, respectively, of nuclease-aptamer complexes 220/320/420. Each of the aptamers preferentially hybridise to the different second nucleotide sequences, specifically, each of aptamers 224/324/424 preferentially hybridise to each of second nucleotide sequences 215/315/415, respectively. Furthermore, each of the nuclease-aptamer complexes 220/320/420 comprise a different nuclease 222/322/422 the activity of which may be separately detected. Specifically, in this embodiment each of nucleases 222/322/422 are restriction endonucleases recognising a different cleavage site.

Panel 3 shows hybridisation between the aptamers 224/324/424 and the second nucleotide sequences 215/315/415. This hybridisation reduces or eliminates inhibition of the nucleases 222/322/422 by the aptamers 224/324/424. As in FIG. 1, this reduction or elimination of inhibition is shown as separation of the aptamers 224/324/424 and nucleases 222/322/422, in part as a conceptual aid. However, as hereinbefore described, a reduction or elimination of inhibition of the nucleases 222/322/422 by the aptamers 224/324/424 may or may not involve actual dissociation between the nucleases 222/322/422 and the aptamers 224/324/424.

In panel 4, the activity of each of the nucleases 222/322/422, can be detected by the cleavage of different reporter nucleic acids. Each of the reporter nucleic acids comprises a different nucleotide sequence, each of which is specifically cleavable by one of the nucleases 222/322/422, respectively.

Each of the reporter nucleic acids also each comprise a different bound fluorophore 234/334/434, and a bound quencher 236/336/436 that serves to quench the fluorescence of each fluorophore 234/334/434. However, cleavage of each of the reporter nucleic acids into fluorophore-containing fragments 238/338/438 and quencher containing fragments 240/340/440, reduces or eliminates quenching of the fluorophores 234/334/434 by the quenchers 236/336/436. Each of the different fluorophores 234/334/434 have distinct emission spectra, such that once released from the action of the quenchers 236/336/436, signals from each of the fluorophores 234/334/434 may be detected separately.

Thus, cleavage of one or more of reporter nucleic acids by the nucleases 222/322/432, respectively, leads to the detection of an individually detectable fluorescent signal from one or more of fluorophores 234/334/434.

EXAMPLE 3

Biosensing Using the EcoRI-Aptamer 3_ADJ_L Complex

In one embodiment, the method of the present invention utilizes a target sequence-specific detection mechanism comprising a linker molecule that switches from an 'inactive' to an 'active' conformation upon hybridisation to a target nucleic acid. In its 'active' conformation, the linker is able to bind to an aptamer in complex with a restriction endonuclease, in this case: EcoRI, and release the endonuclease from aptamer-mediated inhibition. In its 'inactive' conformation, the linker is unable to, or has a significantly reduced ability to, interact with the endonuclease/aptamer complex. When released from inhibition, the nuclease molecule is able to cleave a signaling molecule, thus generating a detectable signal. The system is semi-quantitative, with the signal intensity proportional over a discrete range to the quantity of target nucleic acid molecules in solution.

To demonstrate that the system is applicable to real-world nucleic acid detection situations, synthetic targets were used that represented nucleotide sequences contained within the Cauliflower Mosaic Virus 35S promoter, often indicative in plants of genetic modification, and the genome of *Mycobacterium tuberculosis*, which causes serious infectious disease world-wide.

This embodiment of the biosensor system is modular, with three primary components: a target-detecting linker, a restriction endonuclease/aptamer complex and a molecular break light signaling molecule.

Figure 3:
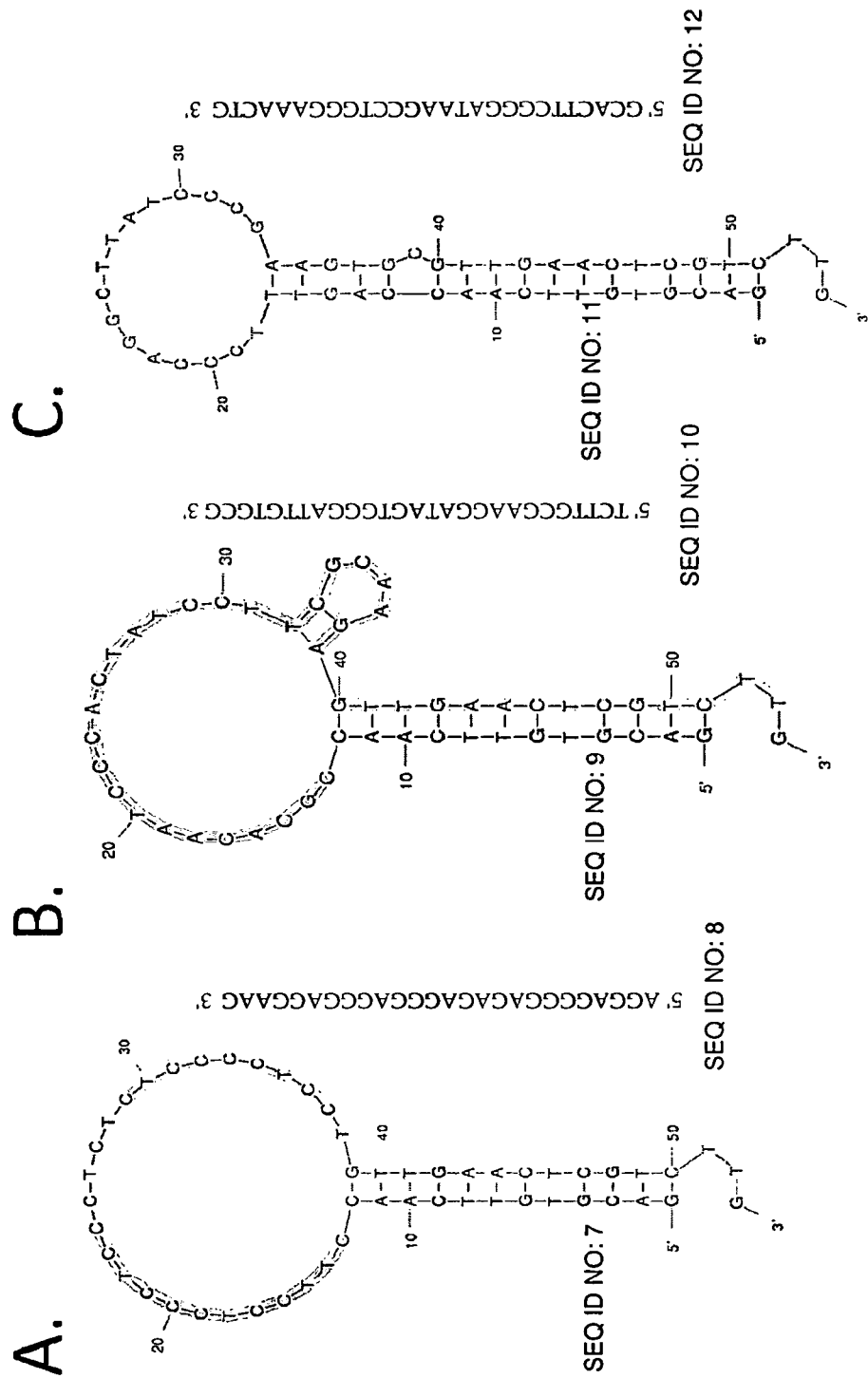
FIG. 3 shows example linker molecules and their targets. A. Arbitrary target-linker (SEQ ID NO:7) and target (SEQ ID NO:8). The target complementary sequence is shaded blue. B. 35S-linker (SEQ ID NO:9)and target (SEQ ID NO:10). The target complementary sequence is shaded green. C. *Mycobacterium tuberculosis*-linker (SEQ ID NO:11)and target (SEQ ID NO:12). The target complementary sequence is shaded yellow. The aptamer binding sequence (trigger moiety) is shaded red in all detectors. The predicted secondary structures were obtained using the MFOLD programme (Zucker, 2003 on the world wide web at frontend .bioinfo.r-pi.edu/applications/mfold/cgi-bin/dna-form 1.cgi).
Figure 4:
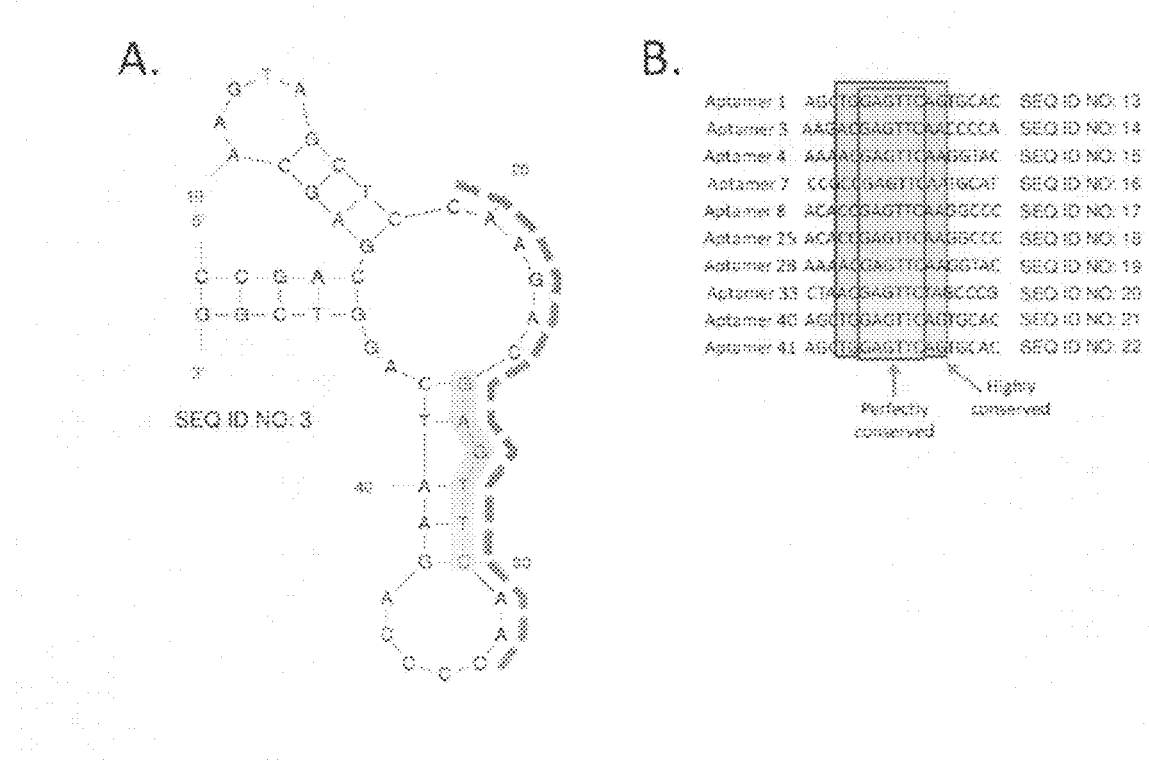
FIG. 4 shows A. Aptamer 3_ADJ_L (SEQ ID NO:3). Apart from removal of a portion of the 5' and 3' primer-binding regions, the aptamer 3_ADJ_L nucleotide sequence is unchanged from that of aptamer 3 identified in the SELEX process. The conserved region prevalent among strong inhibitors of EcoRI is shaded red. The binding site for the trigger moiety of the linker molecule is adjacent to the green dotted line. B. Conserved regions of aptamers that strongly inhibit EcoRI (SEQ ID NOS:13-17, 17, 15, 18, 13 and 13, respectively ). This portion of the aptamer nucleotide sequence is hypothesised to be an element of the primary site mediating inhibition of EcoRI activity.

The target-detection module comprises an oligonucleotide linker that folds into a stable stem/loop hairpin secondary structure, with the loop portion complementary to the target sequence and one strand of the double-stranded stem portion, termed the 'trigger' moiety, complementary to the hypothesised EcoRI binding region of aptamer 3_ADJ_L (FIGS. 3 & 4).

Figure 5:
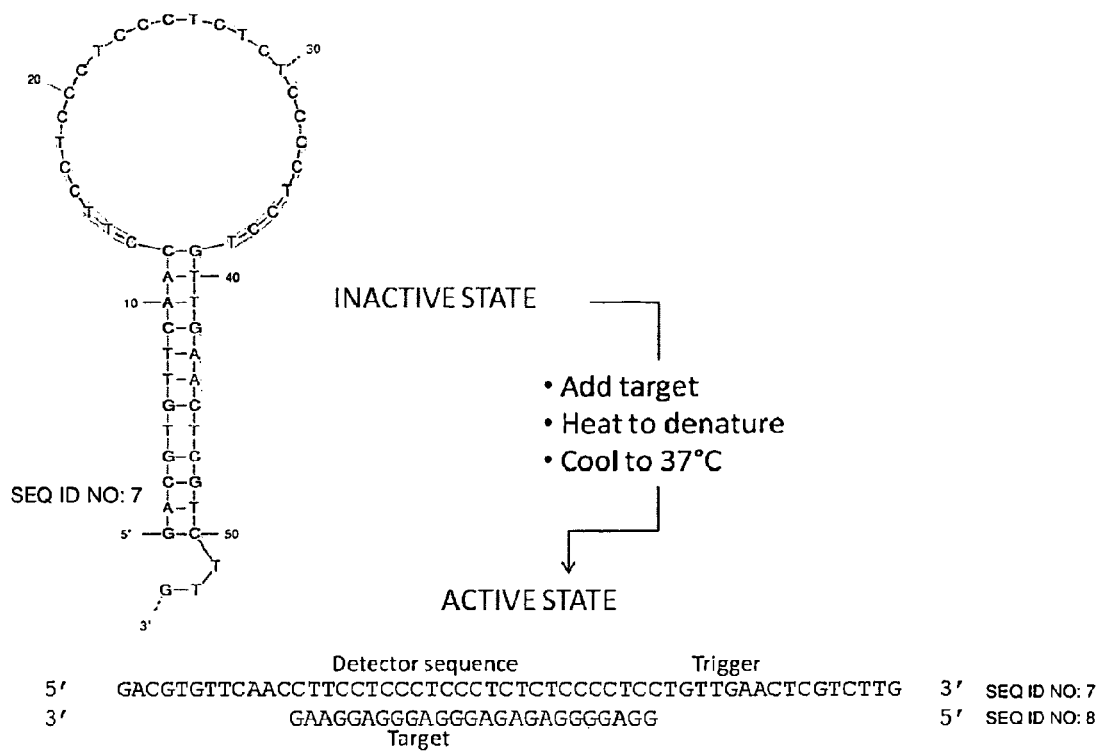
FIG. 5 shows an example of a linker transformed from an inactive to an active state in the presence of a target nucleic acid. In the linker's inactive state (SEQ ID NO:7), the trigger moiety is bound to its complementary stem partner and thus unable to bind to aptamer 3_ADJ_L. In its active state, the target-complementary sequence (SEQ ID NO:7) is bound to a target nucleic acid (SEQ ID NO:19), and the trigger sequence is free to bind to aptamer 3_ADJ_L.

The linker is designed such that the melting temperature of the target-complementary portion of the molecule, when hybridised to the target, is approximately 10° C. higher than the melting temperature of the stem structure containing the trigger moiety. This ensures that when the target nucleic acid is present in solution, the linker binds to the target in preference to reverting to its native stem/loop structure following heat denaturation and cooling. Accordingly, the stem contains a mismatch and the trigger is overhanging, thus allowing the appropriate melting temperature difference to be obtained without the requirement for an excessively long target-complementary sequence (FIG. 5).

Figure 6:
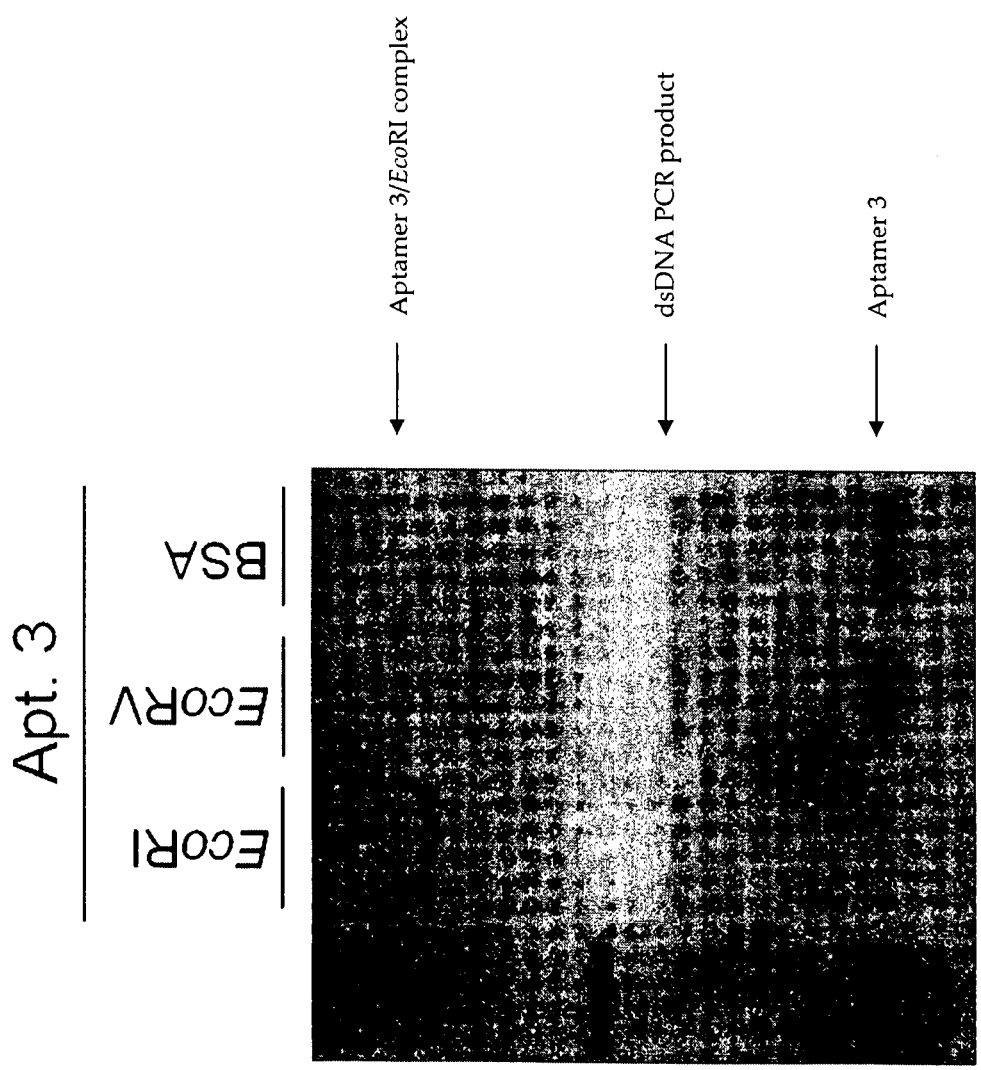
FIG. 6 shows an aptamer 3 gel-shift assay. The asymmetric PCR product derived from aptamer 3 was used. The aptamer 3/EcoRI complex is evident by a high molecular weight band associated with reduced electrophoretic mobility. There is no evidence for similar bands indicating aptamer 3 binding to either the restriction endonuclease EcoRV or bovine serum albumin (BSA).

Numerous unique aptamers that bound strongly and specifically to EcoRI (e.g. FIG. 6) were identified using a SELEX protocol. A majority of the aptamers analysed inhibited the activity of EcoRI to a significant degree. The ideal aptamer for use in the biosensor aptamer/EcoRI complex should not only inhibit EcoRI strongly and specifically, but have secondary and tertiary structures that are amenable to disruption via the hybridisation of the short trigger moiety of the linker molecule.

Many of the EcoRI-inhibiting aptamers identified through SELEX contained a highly-conserved nucleotide sequence hypothesised to bind to the active site of the EcoRI enzyme, possibly due to the conserved region's sequence similarity to the EcoRI recognition site (FIG. 4b). As the predicted aptamer secondary structure in the area of the conserved region contained a mis-match, the site was particularly amenable to denaturation through strand displacement via the binding of a perfectly complementary oligonucleotide of sufficient length. Aptamer 3 was selected as an example of such an aptamer. Based upon the aptamer 3 nucleotide sequence, a modified version with a portion of the SELEX primer binding sites removed (aptamer 3_ADJ_L) was commercially synthesised and formed the basis of the aptamer/EcoRI module for the biosensor.

Upon the linker molecule binding to a target nucleic acid and conforming to its active state, its exposed trigger moiety was able to bind to aptamer 3_ADJ_L. Subsequently, aptamer 3_ADJ_L changed conformation in such a way as to no longer inhibit the activity of EcoRI.

Figure 7:
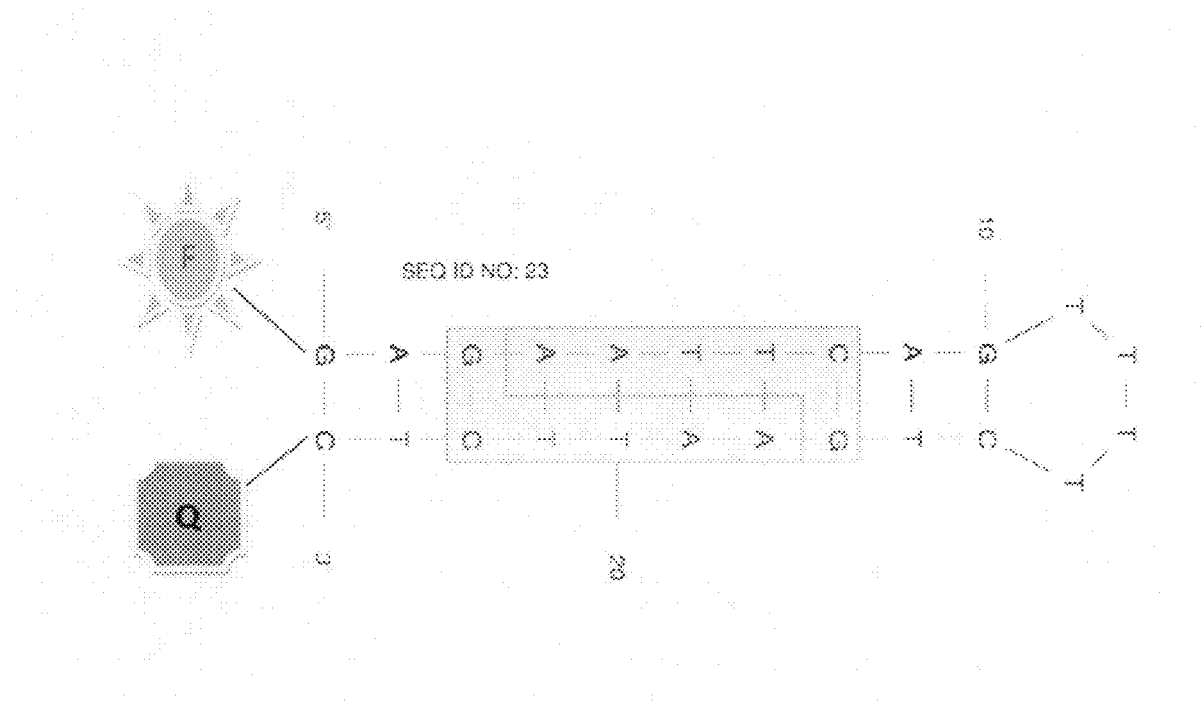
FIG. 7 shows the EcoRI molecular break light (MBL) (SEQ ID NO:20). The predicted stem/loop hairpin secondary structure is shown here. The oligonucleotide comprises a 5' fluorophore and a 3' quencher. The recognition sequence for the restriction endonuclease EcoRI is present within the molecule's stem (shaded red). Upon cleavage by EcoRI, the fluorophore and quencher melt apart and a detectable fluorescent signal is generated.

To detect active EcoRI activity and thus the presence of a target nucleic acid, a modified version of a molecular break light (MBL) molecule (as described in Biggins et al., 2000, supra) served as a signaling module (FIG. 7). The MBL is an oligonucleotide, 5'-labelled with a fluorophore (e.g. FAM) and 3'-labelled with a quencher (e.g. fluorescein). It forms a hairpin stem/loop secondary structure at the temperatures at which EcoRI is active. Due to the close proximity of the fluorophore to the quencher, Förster resonance energy transfer (FRET) ensures that the excited fluorophore's emission is strongly quenched. Within its stem structure is an EcoRI recognition sequence. Upon cleavage by EcoRI, the fluorophore immediately melts away from the quencher and its fluorescent signal is no longer quenched, and thus easily detected. The intensity of the fluorescent signal is proportional to the quantity of break light molecules digested and, therefore, the amount of active EcoRI in solution.

The full biosensor assay is carried out as two sequential reactions. Following addition of a DNA sample to a solution containing the linker, the reaction is heat-denatured and cooled to at least 37° C. The prepared target/linker sample is added to a buffered solution containing the appropriate concentrations of the aptamer/EcoRI complex and MBL, and immediately analysed. Fluorescence measurements were carried out on a RotorGene RG-3000 Real-Time PCR machine operating at a constant temperature of 30° C. or 37° C.

Figure 8:
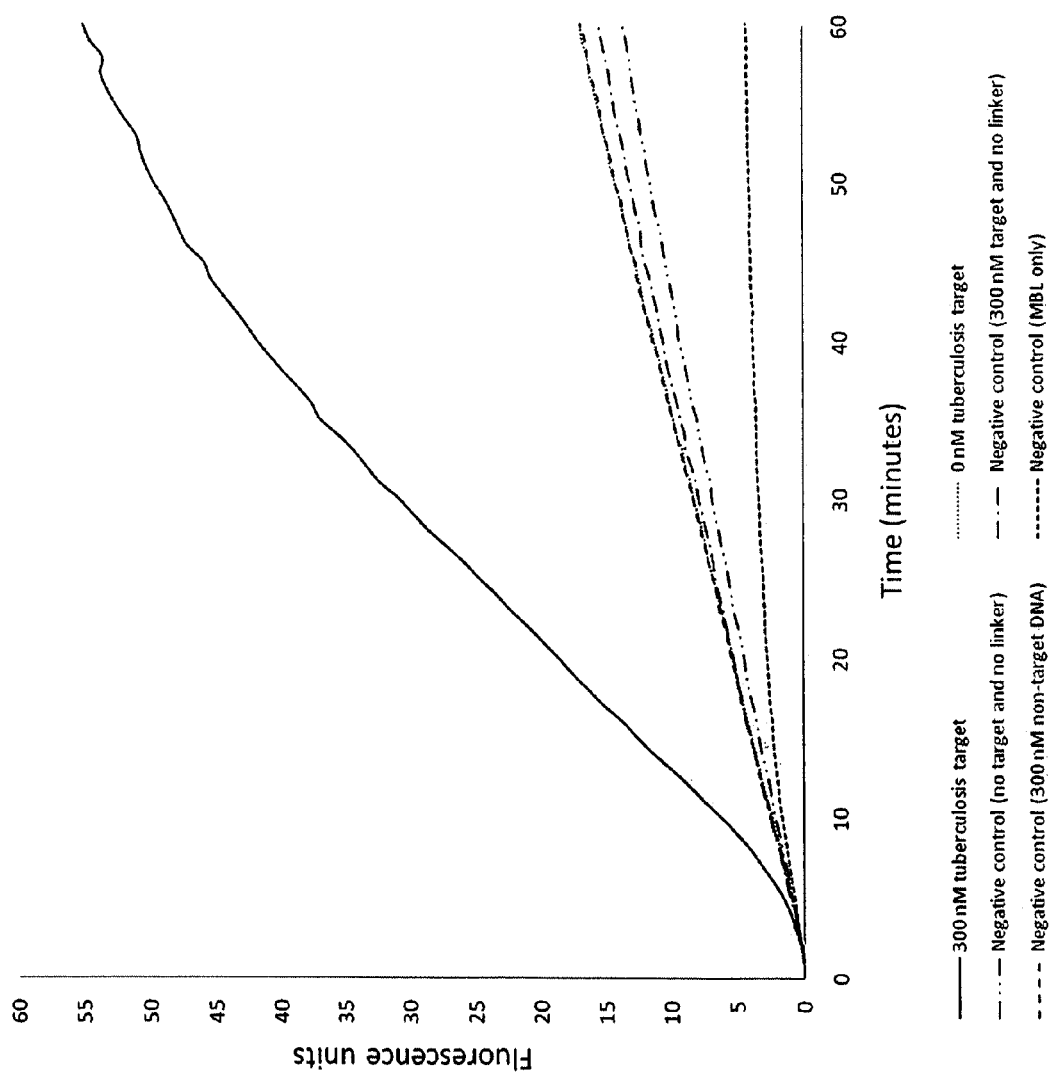
FIG. 8 shows the results of a biosensor assay for a *Mycobacterium tuberculosis* target. Normalised fluorescent output for each treatment is the mean of at least three replicate reactions. The presence of the 300 nM target is clearly discernable from the 0 nM target and 300 nM non-target DNA negative controls after a time period of five minutes.
Figure 9:
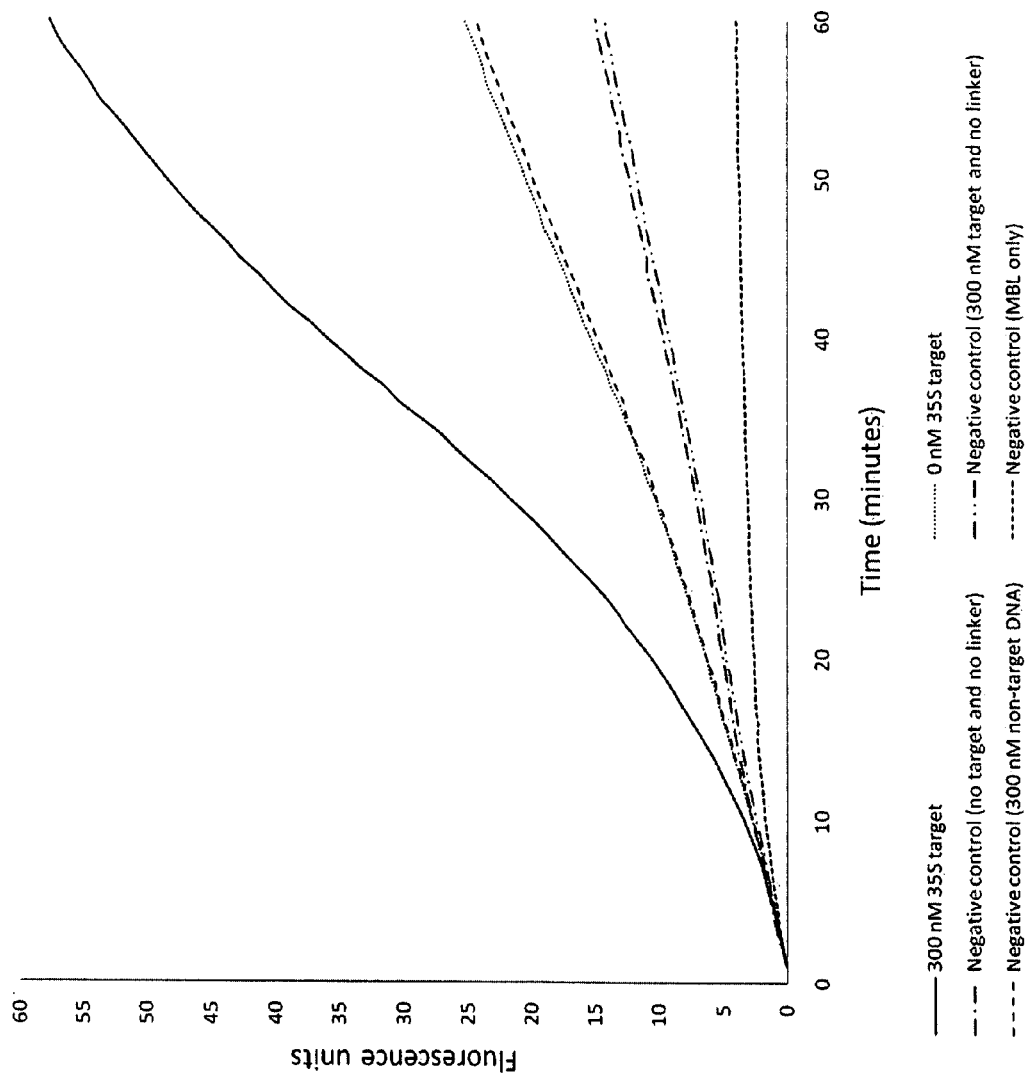
FIG. 9 shows the results of a biosensor assay for a CaMV 35S promoter target. Normalised fluorescent output for each treatment is the mean of four replicate reactions. The presence of the 300 nM target is clearly discernable from the 0 nM target and 300 nM non-target DNA negative controls after a time period of fifteen minutes.
Figure 10:
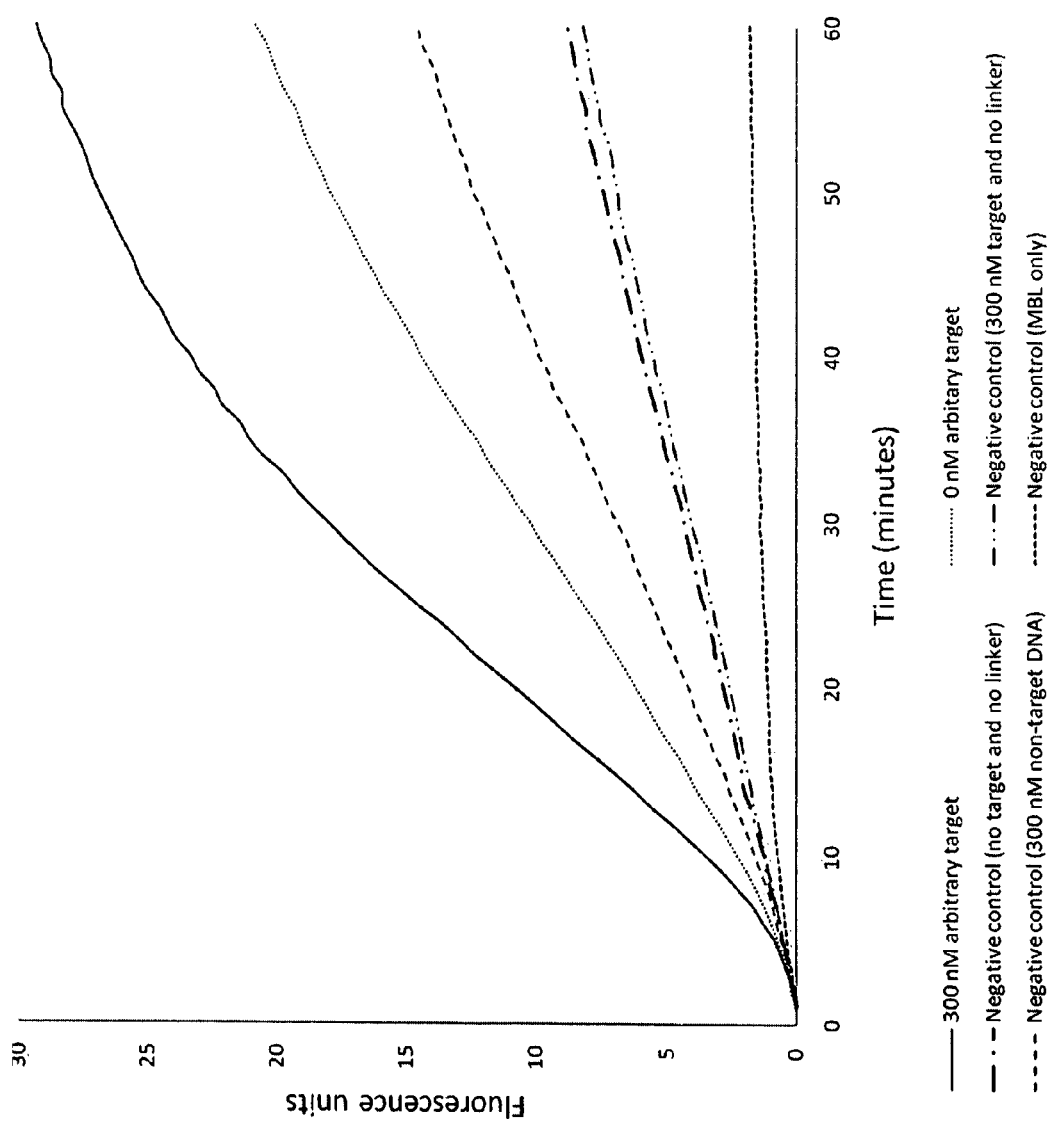
FIG. 10 shows the results of a biosensor assay for an arbitrary target. Normalised fluorescent output for each treatment is the mean of four replicate reactions. The presence of the arbitrary target (300 nM) is clearly discernable from the 0 nM arbitrary target and 300 nM non-target DNA negative controls after a time period of ten minutes.

FIGS. 8, 9, and 10 demonstrate biosensor reaction data where the target is a synthetic *Mycobacterium tuberculosis* target; a synthetic 35S target; and a non-secondary structure-producing arbitrary target, respectively. Controls to demonstrate that the resultant signal is a product of the presence of the target nucleic acid and not an artefact include: a 0-target control; a non-target control, where another non-target oligonucleotide is used to demonstrate specificity; a non-linker control to demonstrate that interaction between the target and linker is specifically releasing EcoRI from inhibition; and a non-target, non-linker control, used to demonstrate the baseline aptamer 3_ADJ_L-inhibited EcoRI activity. The biosensor in its current form is able to specifically detect a nucleic acid target in the low picomole range in a very low assay volume (20 µl.

The primary determinants of the sensitivity of the biosensor system are the detection limits of the instrument used to perform the assay; the time over which the assay is performed; and the degree of background signal present in the assay. Low levels of target-generated signal can easily be rendered undetectable by background fluorescence associated with incomplete aptamer-mediated inhibition of EcoRI and/or the release of EcoRI molecules from inhibition by linkers in their 'inactive' state.

Background fluorescence associated with incompletely inactive linkers is mediated by the stability of the linker molecule's secondary structure. The stem/loop structure of the linker designed against an arbitrary target is less stable at biosensor reaction temperatures (30° C.-37° C.) than those of the 35S and *Mycobacterium tuberculosis* linkers, and a portion of the linker stem melts and exposes the trigger to aptamer 3_ADJ_L hybridisation even in the absence of the target nucleic acid. However, a significant difference in fluorescence intensity between the presence and absence of target nucleic acid is produced after 15 to 20 minutes at the 30° C. reaction temperature. Due to the more stable secondary structures within the target nucleic acid binding sequences of the *Mycobacterium tuberculosis* and 35S linker molecules, these linkers remain inactive at 30° C. and either insignificant or markedly reduced linker-mediated background is present. In each case the presence of 6 picomoles of target is clearly discernable after 15 minutes reaction time.

The second source of background present in all of the biosensor examples is due to incomplete inhibition of EcoRI by aptamer 3_ADJ_L. This is primarily due to a system of simply mixing EcoRI and excess aptamer 3_ADJ_L and binding for 45 minutes at 37° C. before use in a biosensor reaction. Significant amounts of unbound aptamer 3_ADJ_L (which reduces biosensor sensitivity) and unbound EcoRI (which produces background signal) remain. Removal of unbound aptamer/EcoRI and potentially covalently bonding the aptamer to EcoRI is expected to significantly decrease or eliminate this form of background.

Figure 11:
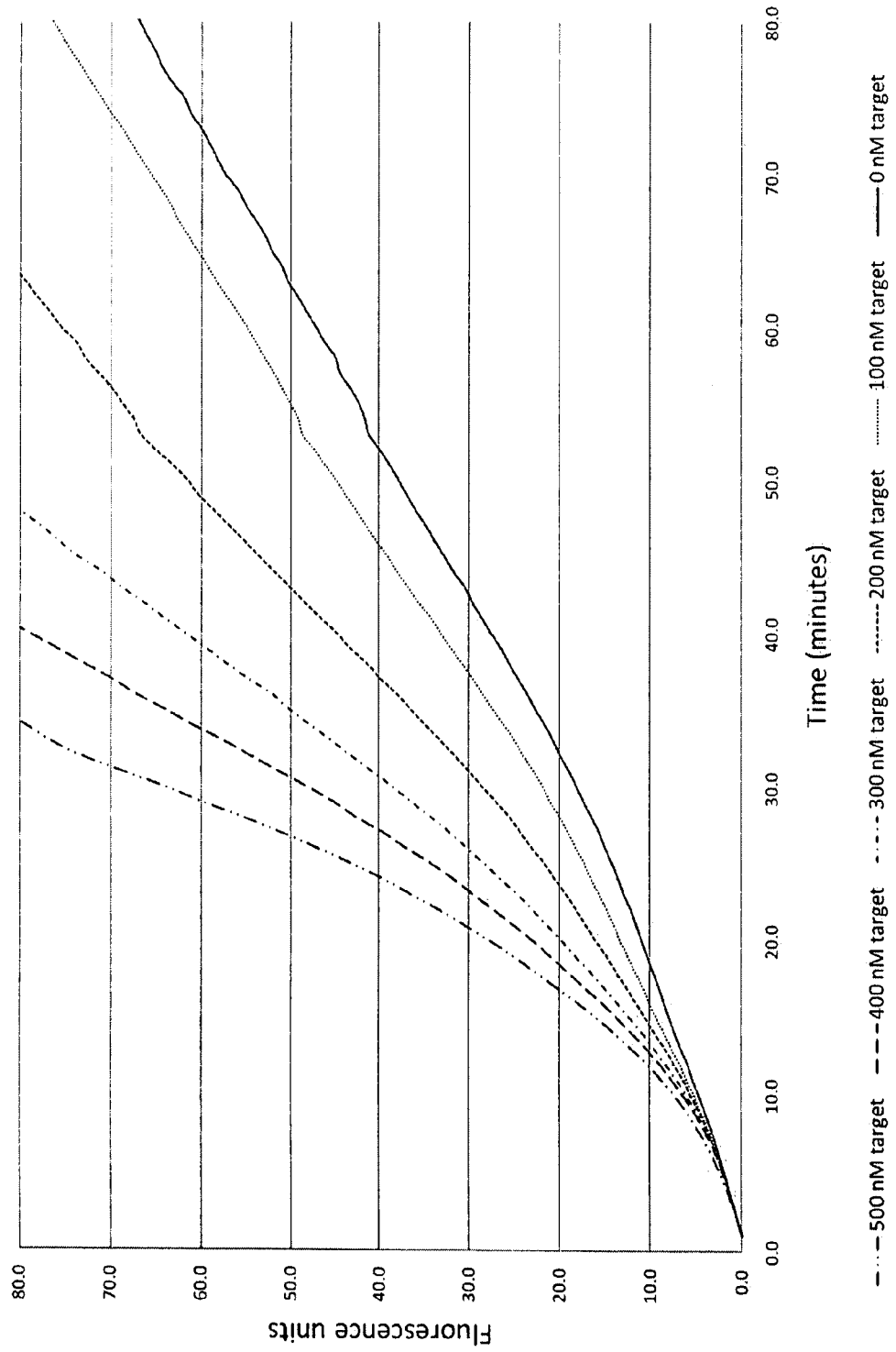
FIG. 11 shows the results of a semi-quantitative biosensor assay. Increasing target (*Mycobacterium tuberculosis*-derived oligonucleotide) concentration from 0 nM to 500 nM results in an increase in signal intensity (fluorescence units) at a given time period. Data are the normalised means of at least two replicate reactions.
Figure 12:
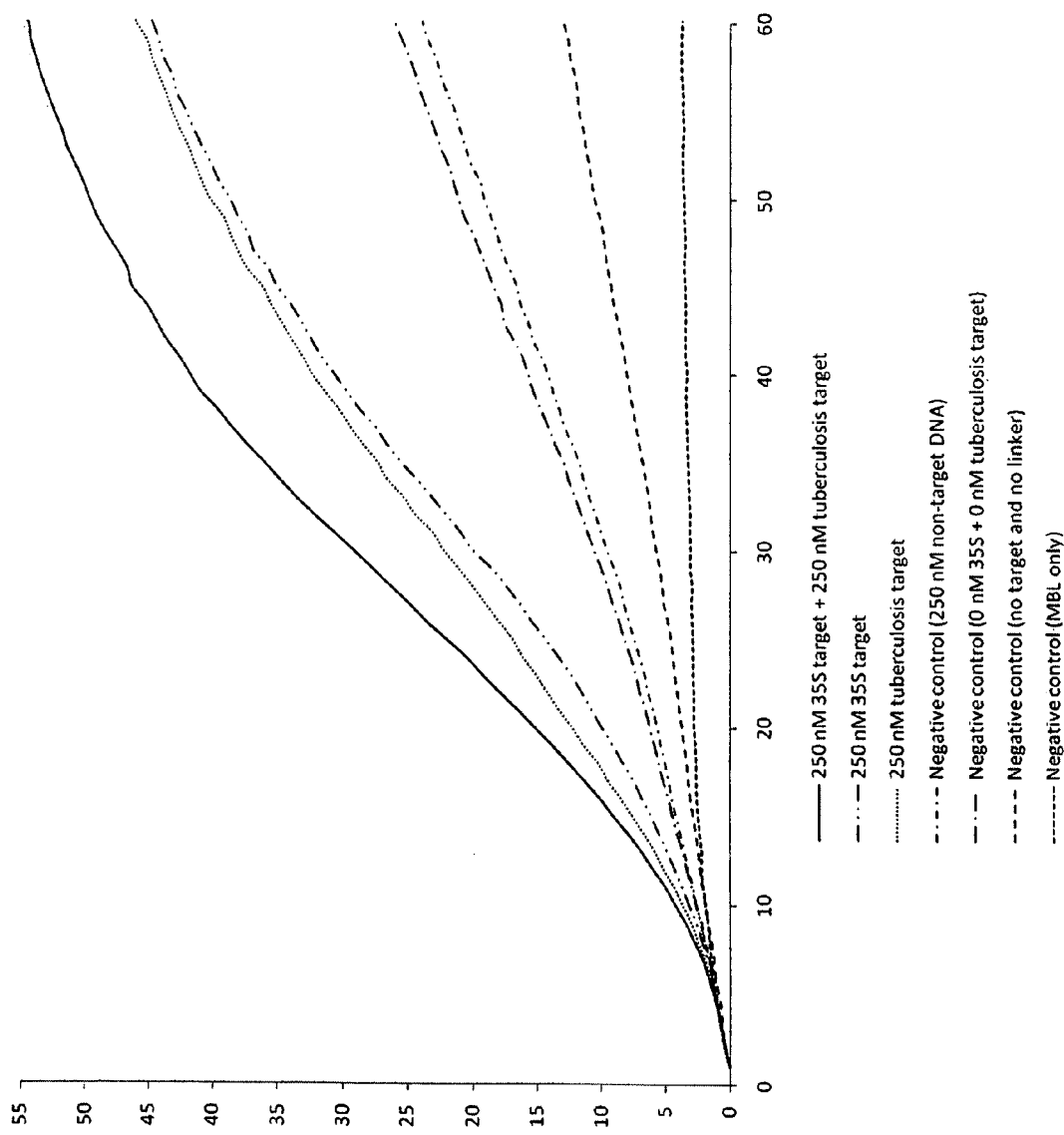
FIG. 12 shows the results of a multiplexed biosensor assay. The presence of either or both of two targets (35S and *Mycobacterium tuberculosis*) was detected simultaneously in a single reaction.

As the intensity of fluorescence is proportional to the amount of target in solution over a certain discrete range, the system is semi-quantitative (FIG. 11). A reduction in background signal will further increase the range in which the system is semi-quantitative.

The use of multiple restriction endonucleases allows for multiplexed target detection to take place concurrently. Under optimal reaction conditions, restriction endonucleases are highly sequence specific, even when multiple enzymes are present in the same digestion reaction. Similarly, multiple unique linkers, aptamer/enzyme complexes and signaling molecules in a single reaction would be expected to specifically and accurately detect the presence of multiple unique target molecules.

Materials and Methods
(i) Selection of EcoRI-Binding Aptamers

DNA aptamers are selected from a random pool using the SELEX (systematic evolution of ligands by exponential enrichment) procedure (see Tuerk and Gold, 1990, supra).

To select aptamers that bind to, and inhibit, the restriction endonuclease EcoRI, a DNA oligonucleotide library (5'-CAAGGCCTCTCCTGATCCGA-40N-GTCGGGAGCT-GAAGCTGCTT-3'; (SEQ ID NO:21) comprising a random 40-mer flanked by 20 base-pair primer binding sites was used. Sequences of oligonucleotide PCR primers for library amplification were 5'-CAAGGCCTCTCCTGATCCGA-3' (SEQ ID NO:22)and 5'-biotin-AAGCAGCTTCAGCTCCCGAC-3'(SEQ ID NO:23). For the 14 rounds of SELEX, a nitrocellulose filter-based binding method was employed (Pileur et al., *Nucleic Acids Research* 31: 5776-5788, 2003). The nitrocellulose filter was able to bind EcoRI and any DNA also bound to EcoRI. A majority of unbound DNA passed freely through the membrane, with a small amount of background retained. Bound DNA was eluted from the filter, amplified, and used in the subsequent round of SELEX.

For each round of SELEX, 4 µg of oligonucleotide library buffered in a 500 µl solution of 50 mM NaCl, 10 mM Tris-HCl pH 8 and 10 mM $MgCl_2$ was used. EcoRI is highly active under these buffering conditions. To allow individual sequences within the oligonucleotide library to conform to their natural secondary structure, the buffered pool was heated to 94° C. for two minutes and immediately placed on ice for 10 minutes. Initially, 4 µL of concentrated EcoRI (New England Biolabs, 100 000 U/ml) was added to the buffered pool, followed by a 20 minute incubation at room temperature. Reduced amounts of EcoRI were added in each subsequent SELEX step. A negative-control solution with no added EcoRI was used in SELEX rounds seven and nine to relatively quantitate recovered EcoRI-bound DNA versus background filter-bound DNA. These mixtures were vacuum-filtered through pre-washed alkali-treated 25 mm 0.45 µM nitrocellulose HAWP filters (Millipore). Following a wash with 3 ml of buffering solution, the bound contents were eluted by crushing the filter in a 400 µl 7 M urea, 50 mM EDTA, 400 mM sodium acetate solution pre-heated to 80° C., and incubating at room temperature for 10 minutes. DNA was precipitated from the supernatant with 800 µl 100% ethanol and 2 µl GlycoBlue (Ambion). The DNA pellets were washed with 1.5 ml 70% ethanol and air-dried prior to re-suspension in 150 µl of 10 mM Tris-HCl pH 8 solution.

To obtain sufficient DNA for the next round of SELEX, recovered DNA was amplified using PCR. Each 100 µl PCR comprised 1 mM of each primer (Sigma-Proligo), 200 dNTPs (Bioline), 1.5 mM $MgCl_2$ (Bioline), 0.5 U Immolase DNA polymerase (Bioline), 1× Immolase DNA polymerase buffer (Bioline) and 10 µl of DNA solution. Cycling conditions for the initial eight rounds were as follows; 7 minutes at 95° C., followed by 30 cycles of 10 seconds at 94° C., 30 seconds at 60° C. and 20 seconds at 72° C. A five minute extension at 72° C. completed the PCR. Following the ninth round of SELEX, adjusted PCR cycling conditions of 7 minutes at 95° C., followed by 15 cycles of 35 seconds at 94° C., 30 seconds at 60° C. and 20 seconds at 72° C., were used to prevent accumulation of non-specific PCR artefacts. For each SELEX round a total of 12 100 W PCRs were performed. All reaction products were subsequently purified with Qiagen MinElute columns, resuspended in 5 µl 10 mM Tris-HCl pH 8 solution and pooled into a total volume of 60 µl. DNA concentrations in these solutions ranged from 500 to 800 ng/µl.

To create single-stranded DNA oligonucleotides from amplified double-stranded DNA, 30 µg of biotinylated PCR product was bound to M-270 streptavidin-coated Dynabeads® (Invitrogen) in 1 M NaCl binding buffer. After washing in binding buffer, the Dynabead®-PCR product complexes were incubated in a 60 µl volume of a 150 mM NaOH solution to break hydrogen bonds binding complementary DNA strands together. The supernatant containing free single-stranded DNA was removed and neutralised with 40 µl of 200 mM HCl and 7.6 W of 1 M Tris-HCl. The neutralised solution was diluted with an additional 400 W of 10 mM Tris-HCl and used in the next round of SELEX.

14 rounds of SELEX were performed in total before PCR products were cloned and sequenced.

(ii) Cloning of EcoRI Binding Aptamers

The PCR products produced in SELEX round 14 were cloned into the pGEM-T Easy vector (Promega) according to the manufacturer's instructions. The plasmids were then transformed into *E. coli* heat shock-competent DH5α cells and grown under ampicillin selection overnight at 37° C. The pGEM-T Easy system allowed for white/blue selection of colonies containing the inserted PCR product.

(iii) Colony and Asymmetric PCRs

To rapidly assay individual aptamers' binding and inhibition efficiency, a colony PCR followed by an asymmetric PCR strategy was used. PCR templates were prepared from colonies by removing a portion of individual colonies with a sterile pipette tip followed by suspension in 100 µl $dH_2O$. These solutions were denatured at 95° C. for 2 minutes and cooled on ice for 10 minutes. 20 µl PCRs were carried out with 1 mM non-biotinylated SELEX forward and reverse primers (Sigma-Proligo), 0.2 mM dNTPs (Bioline), 1× reaction buffer (Bioline), 5% dimethyl sulfoxide (Sigma), 5 U of Immolase DNA polymerase (Bioline) and 2 µl of the prepared PCR template. PCR cycling conditions were the same as those used in the latter stages of the SELEX process.

Upon completion of the colony PCR, reactions were purified using a QIAGEN MinElute PCR purification kit according to the manufacturer's instructions in an effort to remove excess primer and reaction components. PCR products were resuspended in 11 µl of elution buffer.

An asymmetric PCR was performed with the purified PCR products from the colony PCR. Only the sense SELEX forward primer was added which, when extended in the PCR reaction, produces a single-stranded DNA product identical in sequence to the original aptamer. Other PCR reaction conditions were the same as the colony PCR, apart from the omission of dimethyl sulfoxide. Total reaction volume was 100 with 10 µl of the purified PCR product from the colony PCR used. Following completion of the PCR, products were heated to 95° C. for 2 minutes and cooled on ice for 10 minutes to allow the single-stranded aptamers to form their correct secondary structure. Due to incomplete removal of excess primer in the PCR purification reaction, some exponential as well as linear amplification occurred. Accordingly, after 21 cycles of PCR approximately 50% of the product was single-stranded and 50% was double-stranded.

(iv) Gel-Shift Assay

Gel shift assays were performed with individual aptamers generated using the asymmetric PCR protocol. 10 µl of each PCR was added to 300 units of EcoRI (New-England Biolabs) in 1× NEBuffer 1. For selectivity control reactions, the restriction endonuclease EcoRV (New-England Biolabs) or bovine serum albumin (New-England Biolabs) were added instead of EcoRI. Aptamer/ligand binding was carried out for 20 minutes at room temperature. Samples were loaded onto a 10% non-denaturing polyacrylamide gel and electrophoresed at 150V for 1 hour, followed by ethidium bromide staining and viewing on a UV transilluminator (Syngene).

(v) Aptamer Inhibition Test

To determine the EcoRI-inhibition capacity of individual aptamers, 1 µl of asymmetric PCR product was added to 4 units of EcoRI in 1× buffer. Aptamer/EcoRI binding took place at 37° C. for 45 minutes. 4 µl of EcoRI molecular break light (330 nM) was added to each reaction (to a final concentration of 66 nM). Total individual reaction volume was 20 µl. Reactions were then immediately analysed using a Corbett RotorGene RG-3000 operating at a constant temperature of 37° C., with readings taken on the FAM channel at intervals of one minute.

(vi) Sequencing of Plasmids

Inserts from individual plasmids containing aptamer sequences that demonstrated strong EcoRI inhibition were sequenced in the forward and reverse directions using M13 primers and Big Dye Terminator V3.1 reaction mixture (Applied Biosystems) according to the manufacturer's instructions.

(vii) Biosensor Assay

For the biosensor assays, a synthesised version of the strong inhibitor aptamer 3 was used (Sigma-Proligo). The aptamer, aptamer 3_ADJ_L, was identical in sequence to aptamer 3 except for the removal of a portion of both primer binding sites. The total length of aptamer 3_ADJ_L was 49 nucleotides (5'-CCGACGAGCAAGTAGCTCCAAGAC-GAGTTCAACCCCAGAATCAGGTCGG-3'; SEQ ID NO: 3).

Before carrying out the assay, aptamer 3_ADJ_L was bound to EcoRI at a ratio of approximately 40 ng of aptamer to 4 units of EcoRI (New-England Biolabs) in a solution containing 1 µg/µl BSA (New-England Biolabs). Binding took place at 37° C. for 45 minutes.

The linker and target or control DNA at concentrations required for the particular experiment were heated to 95° C. for 2 minutes and then slowly cooled to 4° C. at the rate of 0.1° C./second. The cooled linker/target sample was mixed with the EcoRI (4 U)/aptamer 3_ADJ_L (40 ng) complex and MBL (66 nM) in 1.5×EcoRI NEbuffer. Reactions were analysed in a Corbett RotorGene RG-3000 running at a constant temperature of 30° C. Fluorescence was measured on the FAM channel at intervals of one minute.

(viii) Semi-Quantitative Biosensor Assay

The semi-quantitative biosensor assay was carried out as per the biosensor assay except for the addition of higher concentrations of EcoRI (8 U)/aptamer 3_ADJ_L (80 ng) and MBL (122 nM) to the assay. The *Mycobacterium tuberculosis* linker and target were used. Target concentrations in the final reaction were 0 nM, 100 nM, 200 nM, 300 nM, 400 nM and 500 nM.

(ix) Multiplexed Biosensor Assay

The multiplexed biosensor assay was carried out as per the biosensor assay except for the addition of higher concentrations of EcoRI (7 U)/aptamer 3_ADJ_L (53 ng) and MBL (100 nM) to the assay. The *Mycobacterium tuberculosis* linker and the 35S linker were present in the target binding reaction. Five picomoles of the 35S and/or *Mycobacterium tuberculosis* target nucleic adds were added to each reaction at a final concentration of 250 nM.

Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of the steps or features.

The claims defining the invention are as follows:

1. A method for detecting a target nucleotide sequence in a sample, the method comprising:

providing a nuclease-aptamer complex as set forth in FIG. 1, the complex comprising a nuclease bound to an aptamer, wherein binding of the aptamer to the nuclease inhibits the activity of the nuclease;

providing a linker nucleic acid comprising a first portion which can hybridise with the target nucleotide sequence if it is present in the sample, and a second portion which can hybridise with the aptamer when the first portion of the linker nucleic acid is hybridised to the target nucleotide sequence, wherein hybridisation between the aptamer and the second portion of the linker nucleic acid modifies, reduces or eliminates binding between the aptamer and the nuclease, and wherein the linker nucleic acid comprises a stem loop structure and at least a portion of the first portion of the linker is comprised within a loop of the stem-loop structure and at least a portion of the second portion of the linker is comprised within a stem of the stem-loop structure;

applying the nuclease-aptamer complex to the sample;

applying the linker nucleic acid to the sample;

allowing the first portion of the linker nucleic acid to hybridise with the target nucleotide sequence if it is present in the sample;

allowing the second portion of the linker nucleic acid to hybridise with the aptamer when the first portion of the linker nucleic acid hybridises with the target nucleotide sequence; and detecting the activity of the nuclease, wherein increased nuclease activity in the sample is indicative of the presence of the target nucleotide sequence in the sample.

2. The method of claim 1 wherein the method comprises a reaction for simultaneously detecting a plurality of target nucleotide sequences in a sample, and the method comprises:

providing a plurality of linker nucleic acids at least two of which comprise different first portions which can hybridise to different target nucleotide sequences and also comprise different second portions which can hybridise with different aptamers; and providing a plurality of nuclease-aptamer complexes according to FIG. 2, wherein at least two of the nuclease-aptamer complexes comprise aptamers which preferentially hybridise to the different second portions of the linker nucleic acids and comprise different nucleases, the activity of which may be separately detected.

3. The method of claim 1, wherein the method comprises a method for simultaneously detecting a plurality of target nucleotide sequences in a sample, and the method comprises:

providing a plurality of linker nucleic acids at least two of which comprise different first portions which can hybridise to different target nucleotide sequences but wherein the linker nucleic acids comprise second portions which can hybridise with the same aptamer; and providing a nuclease-aptamer complex comprising an aptamer which can hybridise with the second portions of the linker nucleic acids.

4. The method of claim 1 wherein the activity of the nuclease is determined by the rate or extent of cleavage of a reporter nucleic acid.

5. The method of claim 1 wherein the nuclease of the nuclease-aptamer complex is a restriction endonuclease.

6. The method of claim 4 wherein a fluorophore is bound to the reporter nucleic acid and a quencher, which quenches the fluorescence of the fluorophore, is also bound to the reporter nucleic acid, wherein cleavage of the reporter nucleic acid by the nuclease reduces or eliminates the quenching of the fluorophore by the quencher.

7. The method of claim 4, wherein a polypeptide is bound to the reporter nucleic acid and an immobilisable agent is bound to the reporter nucleic acid, wherein cleavage of the reporter nucleic acid releases the polypeptide from the immobilisable agent such that after immobilisation of the immobilisable agent, the amount of non-immobilised polypeptide is indicative of the activity of the nuclease.

8. The method of claim 7, wherein the immobilisable agent is a magnetic bead and immobilisation of the immobilisable agent is effected by the application of a magnetic field.

9. The method of claim 1 wherein the target nucleotide sequence is a non-native nucleotide sequence in the organism.

10. The method of claim 9, wherein the target nucleotide sequence is a genomic nucleotide sequence, an allele nucleotide sequence, a mutant nucleotide sequence, a single nucleotide polymorphism, a transposon nucleotide sequence or a viral nucleotide sequence.

11. The method of claim 1 wherein the sample is a plant sample.

12. The method of claim 1 wherein the nuclease of the nuclease-aptamer complex is EcoRI.

* * * * *

SEQUENCE LISTING

```
<160> NUMBER OF SEQ ID NOS: 23

<210> SEQ ID NO 1
<211> LENGTH: 6
<212> TYPE: DNA
<213> ORGANISM: Artificial Sequence
<220> FEATURE:
<223> OTHER INFORMATION: synthetic EcoRI-binding aptamer nucleotide
      sequence motif 1

<400> SEQUENCE: 1 gagttc                                                                    6

<210> SEQ ID NO 2
<211> LENGTH: 10
<212> TYPE: DNA
<213> ORGANISM: Artificial Sequence
<220> FEATURE:
<223> OTHER INFORMATION: synthetic EcoRI-binding aptamer nucleotide
      sequence motif 2

<400> SEQUENCE: 2 hsgagttcwr                                                               10

<210> SEQ ID NO 3
<211> LENGTH: 49
<212> TYPE: DNA
```

-continued

```
<213> ORGANISM: Artificial Sequence
<220> FEATURE:
<223> OTHER INFORMATION: synthetic EcoRI-binding Aptamer 3_ADJ_L
      nucleotide sequence

<400> SEQUENCE: 3
ccgacgagca agtagctcca agacgagttc aaccccagaa tcaggtcgg              49

<210> SEQ ID NO 4
<211> LENGTH: 15
<212> TYPE: DNA
<213> ORGANISM: Artificial Sequence
<220> FEATURE:
<223> OTHER INFORMATION: synthetic EcoRI-binding Aptamer 3_ADJ_L-binding
      nucleotide sequence

<400> SEQUENCE: 4
gttgaactgg tcttg                                                   15

<210> SEQ ID NO 5
<211> LENGTH: 27
<212> TYPE: DNA
<213> ORGANISM: Artificial Sequence
<220> FEATURE:
<223> OTHER INFORMATION: synthetic Cauliflower Mosaic Virus (CaMV) 35S
      promoter targeting nucleotide sequence

<400> SEQUENCE: 5
cgcacaatcc cactatcctt cgcaaga                                      27

<210> SEQ ID NO 6
<211> LENGTH: 27
<212> TYPE: DNA
<213> ORGANISM: Artificial Sequence
<220> FEATURE:
<223> OTHER INFORMATION: synthetic Mycobacterium tuberculosis targeting
      nucleotide sequence

<400> SEQUENCE: 6
cagtttccca ggcttatccc gaagtgc                                      27

<210> SEQ ID NO 7
<211> LENGTH: 53
<212> TYPE: DNA
<213> ORGANISM: Artificial Sequence
<220> FEATURE:
<223> OTHER INFORMATION: synthetic arbitrary target-linker aptamer
      nucleotide sequence, biosensor system
      target-detection module
<221> NAME/KEY: misc_feature
<222> LOCATION: (13)...(38)
<223> OTHER INFORMATION: target complementary sequence, detector
      sequence
<221> NAME/KEY: misc_feature
<222> LOCATION: (39)...(53)
<223> OTHER INFORMATION: aptamer binding sequence, trigger moiety

<400> SEQUENCE: 7
gacgtgttca accttcctcc ctccctctct cccctcctgt tgaactcgtc ttg         53

<210> SEQ ID NO 8
<211> LENGTH: 26
<212> TYPE: DNA
<213> ORGANISM: Artificial Sequence
<220> FEATURE:
<223> OTHER INFORMATION: synthetic arbitrary aptamer target sequence

<400> SEQUENCE: 8
```
aggaggggag agagggaggg aggaag                                              26

```
<210> SEQ ID NO 9
<211> LENGTH: 54
<212> TYPE: DNA
<213> ORGANISM: Artificial Sequence
<220> FEATURE:
<223> OTHER INFORMATION: synthetic Cauliflower Mosaic Virus (CaMV)
      35S-linker nucleotide sequence
<221> NAME/KEY: misc_feature
<222> LOCATION: (13)...(39)
<223> OTHER INFORMATION: target complementary sequence
<221> NAME/KEY: misc_feature
<222> LOCATION: (40)...(54)
<223> OTHER INFORMATION: aptamer binding sequence, trigger moiety

<400> SEQUENCE: 9
```
gacgtgttca accgcacaat cccactatcc ttcgcaagag ttgaactcgt cttg              54

```
<210> SEQ ID NO 10
<211> LENGTH: 27
<212> TYPE: DNA
<213> ORGANISM: Artificial Sequence
<220> FEATURE:
<223> OTHER INFORMATION: synthetic Cauliflower Mosaic Virus (CaMV)
      35S-linker target sequence

<400> SEQUENCE: 10
```
tcttgcgaag gatagtggga ttgtgcg                                            27

```
<210> SEQ ID NO 11
<211> LENGTH: 54
<212> TYPE: DNA
<213> ORGANISM: Artificial Sequence
<220> FEATURE:
<223> OTHER INFORMATION: synthetic Mycobacterium tuberculosis-linker
      nucleotide sequence
<221> NAME/KEY: misc_feature
<222> LOCATION: (13)...(39)
<223> OTHER INFORMATION: target complementary sequence
<221> NAME/KEY: misc_feature
<222> LOCATION: (40)...(54)
<223> OTHER INFORMATION: aptamer binding sequence, trigger moiety

<400> SEQUENCE: 11
```
gacgtgttca accagtttcc caggcttatc ccgaagtgcg ttgaactcgt cttg              54

```
<210> SEQ ID NO 12
<211> LENGTH: 27
<212> TYPE: DNA
<213> ORGANISM: Artificial Sequence
<220> FEATURE:
<223> OTHER INFORMATION: synthetic Mycobacterium tuberculosis-linker
      target sequence

<400> SEQUENCE: 12
```
gcacttcggg ataagcctgg gaaactg                                            27

```
<210> SEQ ID NO 13
<211> LENGTH: 18
<212> TYPE: DNA
<213> ORGANISM: Artificial Sequence
<220> FEATURE:
<223> OTHER INFORMATION: synthetic conserved region inhibiting EcoRI
      from Aptamer 1, Aptamer 40 and Aptamer 41

<400> SEQUENCE: 13
```
agctggagtt cagtgcac                                                      18

```
<210> SEQ ID NO 14
<211> LENGTH: 18
<212> TYPE: DNA
<213> ORGANISM: Artificial Sequence
<220> FEATURE:
<223> OTHER INFORMATION: synthetic conserved region inhibiting EcoRI
      from Aptamer 3

<400> SEQUENCE: 14
aagacgagtt caacccca                                                   18

<210> SEQ ID NO 15
<211> LENGTH: 18
<212> TYPE: DNA
<213> ORGANISM: Artificial Sequence
<220> FEATURE:
<223> OTHER INFORMATION: synthetic conserved region inhibiting EcoRI
      from Aptamer 4 and Aptamer 28

<400> SEQUENCE: 15
aaaacgagtt caaggtac                                                   18

<210> SEQ ID NO 16
<211> LENGTH: 18
<212> TYPE: DNA
<213> ORGANISM: Artificial Sequence
<220> FEATURE:
<223> OTHER INFORMATION: synthetic conserved region inhibiting EcoRI
      from Aptamer 7

<400> SEQUENCE: 16
ccgccgagtt caatgcat                                                   18

<210> SEQ ID NO 17
<211> LENGTH: 18
<212> TYPE: DNA
<213> ORGANISM: Artificial Sequence
<220> FEATURE:
<223> OTHER INFORMATION: synthetic conserved region inhibiting EcoRI
      from Aptamer 8 and Aptamer 25

<400> SEQUENCE: 17
acaccgagtt caaggccc                                                   18

<210> SEQ ID NO 18
<211> LENGTH: 18
<212> TYPE: DNA
<213> ORGANISM: Artificial Sequence
<220> FEATURE:
<223> OTHER INFORMATION: synthetic conserved region inhibiting EcoRI
      from Aptamer 33

<400> SEQUENCE: 18
ctaacgagtt ctagcccg                                                   18

<210> SEQ ID NO 19
<211> LENGTH: 25
<212> TYPE: DNA
<213> ORGANISM: Artificial Sequence
<220> FEATURE:
<223> OTHER INFORMATION: synthetic aptamer 3_ADJ_L target sequence

<400> SEQUENCE: 19 ggagggggaga gagggaggga ggaag                                          25

<210> SEQ ID NO 20
```

```
<211> LENGTH: 24
<212> TYPE: DNA
<213> ORGANISM: Artificial Sequence
<220> FEATURE:
<223> OTHER INFORMATION: synthetic EcoRI molecular break light (MBL)
      nucleotide sequence
<221> NAME/KEY: modified_base
<222> LOCATION: (1)...(1)
<223> OTHER INFORMATION: g 5' modified by fluorophore
<221> NAME/KEY: modified_base
<222> LOCATION: (24)...(24)
<223> OTHER INFORMATION: c 3' modified by quencher

<400> SEQUENCE: 20
gagaattcag ttttctgaat tctc                                            24

<210> SEQ ID NO 21
<211> LENGTH: 80
<212> TYPE: DNA
<213> ORGANISM: Artificial Sequence
<220> FEATURE:
<223> OTHER INFORMATION: synthetic random 40-mer flanked by primer
      binding sites for selection of EcoRI-binding aptamers
<221> NAME/KEY: modified_base
<222> LOCATION: (21)...(60)
<223> OTHER INFORMATION: n = g, a, c or t

<400> SEQUENCE: 21
caaggcctct cctgatccga nnnnnnnnnn nnnnnnnnnn nnnnnnnnnn nnnnnnnnnn     60
gtcgggagct gaagctgctt                                                 80

<210> SEQ ID NO 22
<211> LENGTH: 20
<212> TYPE: DNA
<213> ORGANISM: Artificial Sequence
<220> FEATURE:
<223> OTHER INFORMATION: synthetic oligonucleotide PCR primer for
      library amplification

<400> SEQUENCE: 22
caaggcctct cctgatccga                                                 20

<210> SEQ ID NO 23
<211> LENGTH: 20
<212> TYPE: DNA
<213> ORGANISM: Artificial Sequence
<220> FEATURE:
<223> OTHER INFORMATION: synthetic oligonucleotide PCR primer for
      library amplification
<221> NAME/KEY: modified_base
<222> LOCATION: (1)...(1)
<223> OTHER INFORMATION: a modified by biotin

<400> SEQUENCE: 23
aagcagcttc agctcccgac                                                 20
```